United States Patent
Rengifo et al.

(10) Patent No.: US 9,044,729 B2
(45) Date of Patent: Jun. 2, 2015

(54) METHODS AND DEVICES FOR ELECTROMAGNETIC AMPLIFICATION OF NUCLEIC ACIDS

(71) Applicants: Raul Cuero Rengifo, Cypress, TX (US); Mario Antonio Franco Jimenez, Manizales (CO); Natalia Gutierrez Calle, Manizales (CO); Mariana Sanchez Londono, Manizales (CO)

(72) Inventors: Raul Cuero Rengifo, Cypress, TX (US); Mario Antonio Franco Jimenez, Manizales (CO); Natalia Gutierrez Calle, Manizales (CO); Mariana Sanchez Londono, Manizales (CO)

(73) Assignee: International Park of Creativity, Bogota (CO)

( * ) Notice: Subject to any disclaimer, the term of this patent is extended or adjusted under 35 U.S.C. 154(b) by 0 days.

(21) Appl. No.: 13/839,325

(22) Filed: Mar. 15, 2013

(65) Prior Publication Data
US 2014/0030764 A1   Jan. 30, 2014

Related U.S. Application Data

(60) Provisional application No. 61/676,358, filed on Jul. 27, 2012.

(51) Int. Cl.
  *C12P 19/34* (2006.01)
  *B01J 19/08* (2006.01)
  *C12Q 1/68* (2006.01)

(52) U.S. Cl.
  CPC .............. *B01J 19/087* (2013.01); *C12P 19/34* (2013.01); *C12Q 1/686* (2013.01)

(58) Field of Classification Search
  CPC ..................................................... C12P 19/34
  USPC ....................................................... 435/91.2
  See application file for complete search history.

(56) References Cited

U.S. PATENT DOCUMENTS

| | | | |
|---|---|---|---|
| 5,645,801 A | 7/1997 | Bouma et al. | |
| 5,646,019 A | 7/1997 | Nielson et al. | |
| 6,013,459 A | 1/2000 | Meade | |
| 6,197,563 B1 | 3/2001 | Erlich et al. | |
| 7,087,148 B1 | 8/2006 | Blackburn et al. | |
| 7,820,454 B2 * | 10/2010 | Su et al. | 436/526 |
| 2004/0053290 A1 * | 3/2004 | Terbrueggen et al. | 435/6 |
| 2008/0268529 A1 | 10/2008 | Furusato et al. | |
| 2009/0025489 A1 * | 1/2009 | Christensen et al. | 73/864 |
| 2009/0246834 A1 | 10/2009 | Goel | |
| 2010/0184020 A1 * | 7/2010 | Beer | 435/6 |
| 2010/0216126 A1 | 8/2010 | Balachandran et al. | |
| 2011/0068789 A1 | 3/2011 | Hwang | |

FOREIGN PATENT DOCUMENTS

| | | |
|---|---|---|
| WO | 9617959 | 6/1996 |
| WO | 2010114842 A1 | 10/2010 |
| WO | 2012145449 | 10/2012 |

OTHER PUBLICATIONS

International Search Report dated Jul. 2, 2012 for application PCT/US12/34154.
International Search Report dated Jan. 31, 2014 for application PCT/US2013/052453.

* cited by examiner

*Primary Examiner* — Ardin Marschel
(74) *Attorney, Agent, or Firm* — Gardner Groff Greenwald & Villanueva, PC

(57) ABSTRACT

Methods and devices for amplifying nucleic acids generally involve exposing the nucleic acid to an electromagnetic field, for example a mini-current magnetic field, while performing the steps of PCR. The PCR methods and devices provide numerous advantages over conventional PCR techniques and systems such as reduced reaction times, no heating requirements, and reduced amounts of reagents (e.g., optional use polymerases and primers). Additionally, the PCR methods and devices require significantly shorter reaction times (e.g., less than one hour) compared to conventional PCR techniques and systems (minimum 2 hours). Finally, as shown in the Examples, the PCR methods and devices amplify significantly more DNA compared to conventional PCR techniques and systems. Accordingly, the PCR methods and devices provide a more efficient and cost-effective way to perform PCR when compared to conventional PCR techniques and systems.

19 Claims, 27 Drawing Sheets

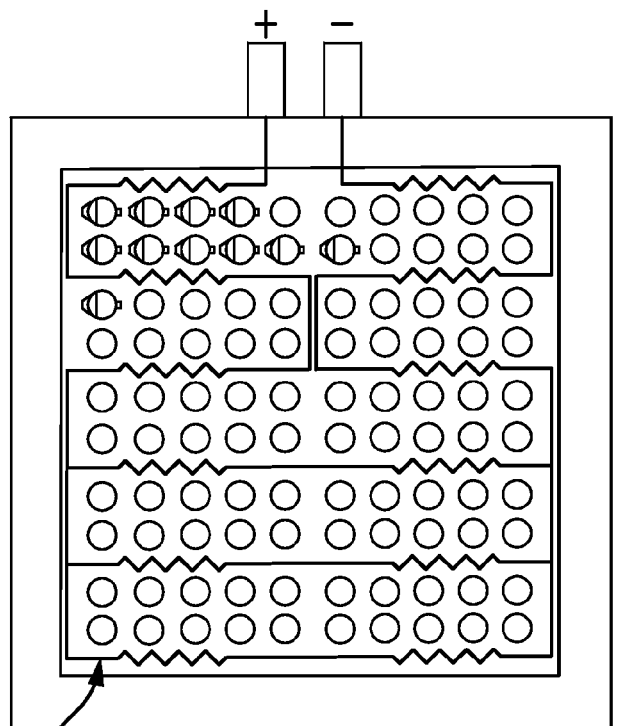
54c(i) FIG. 12A
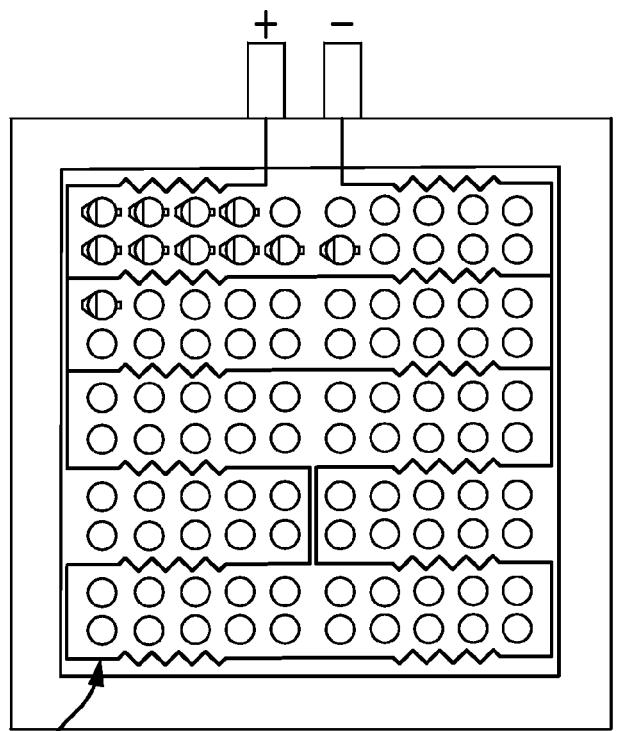
54c(ii) FIG. 12B

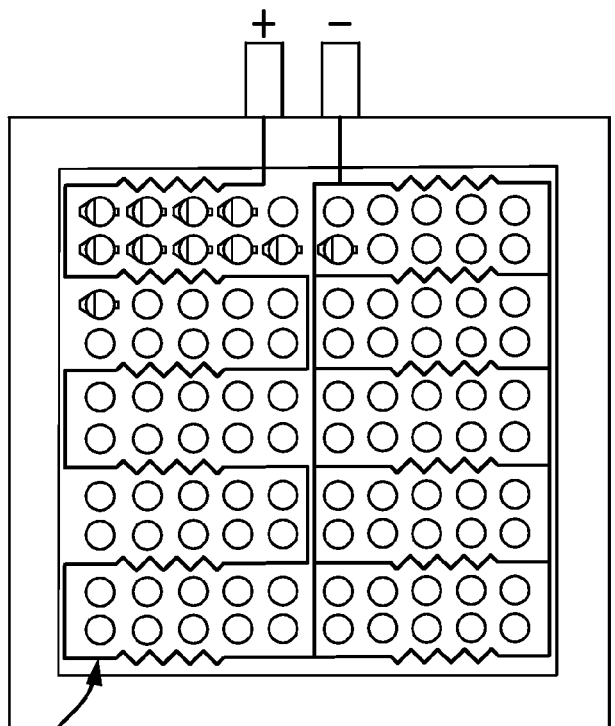
54c(iii)  FIG. 12C
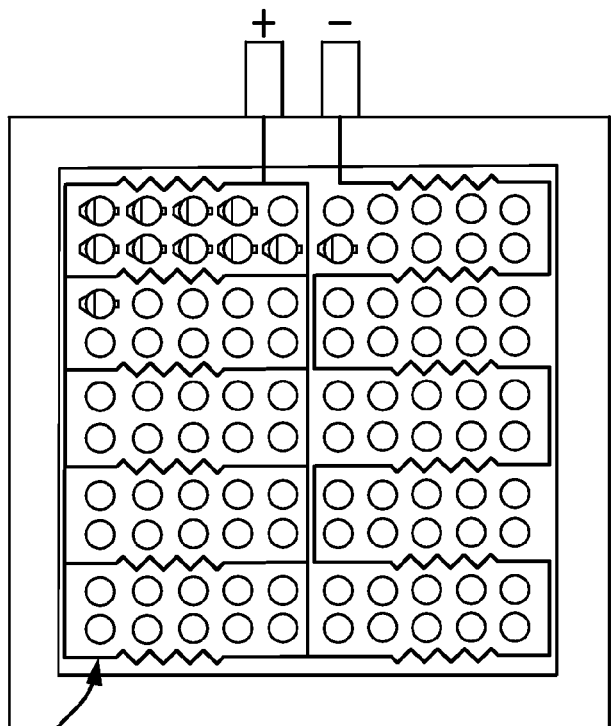
54c(iv)  FIG. 12D

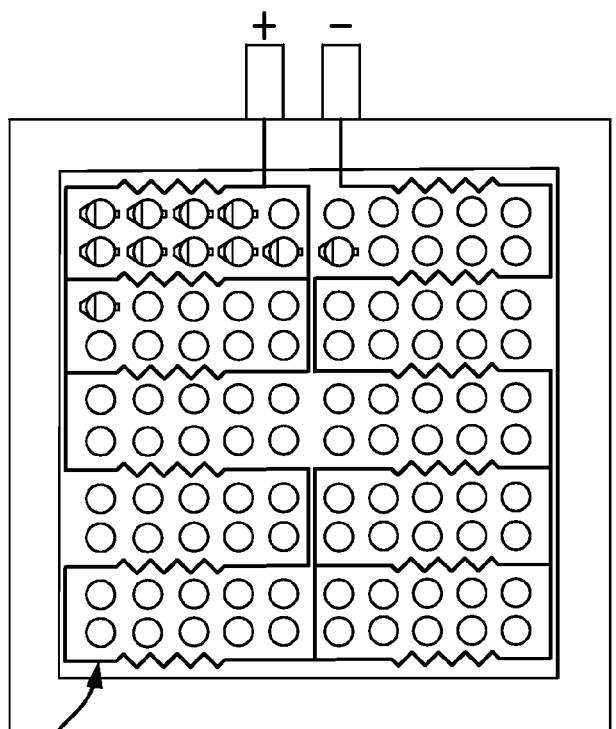
54c(v)  FIG. 12E
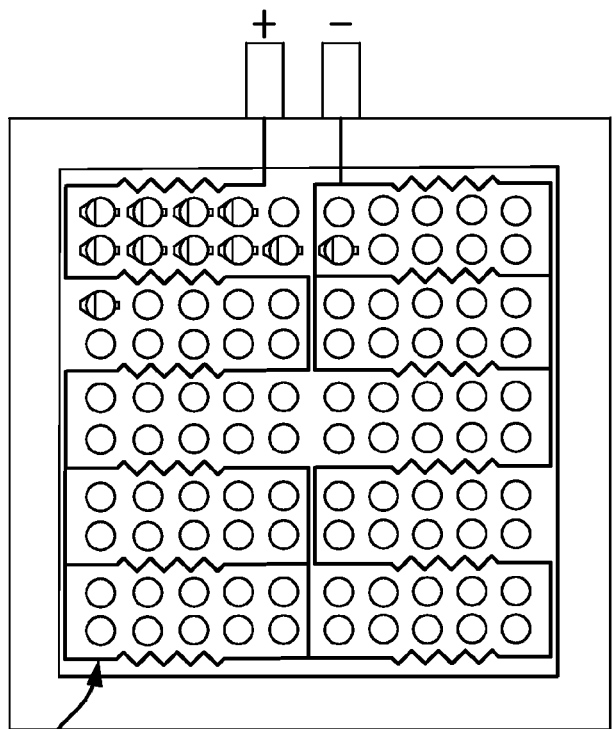
54c(vi)  FIG. 12F

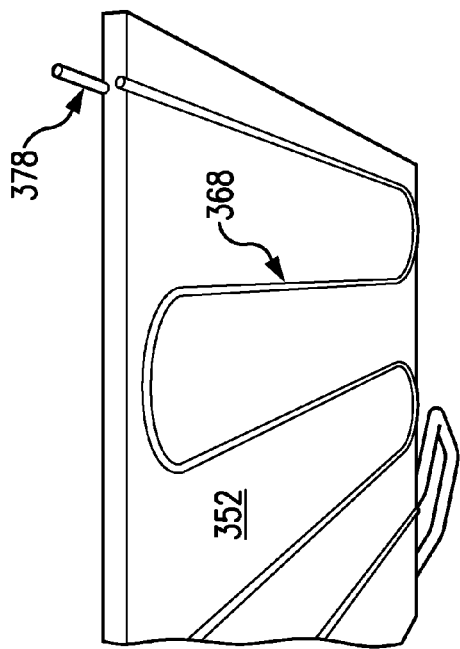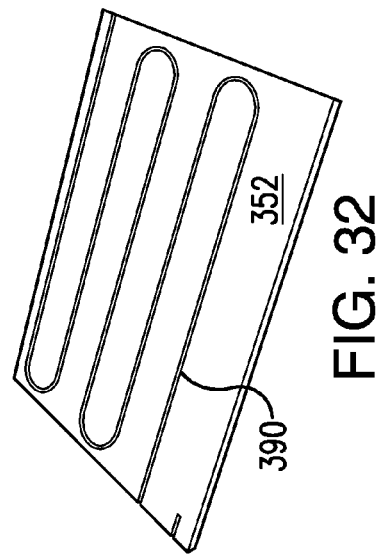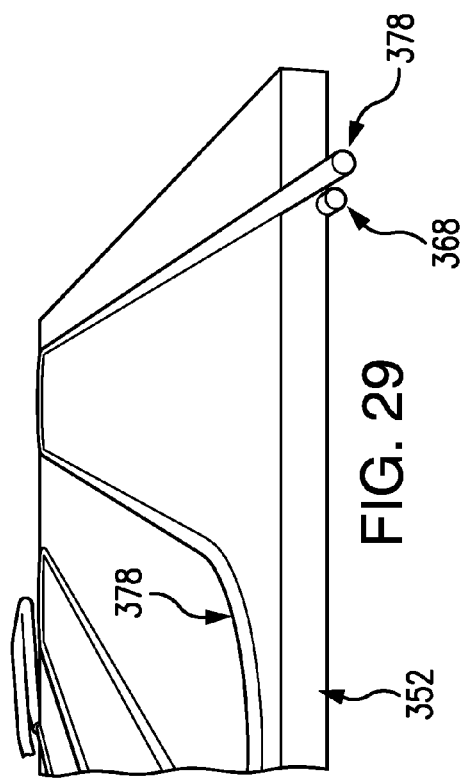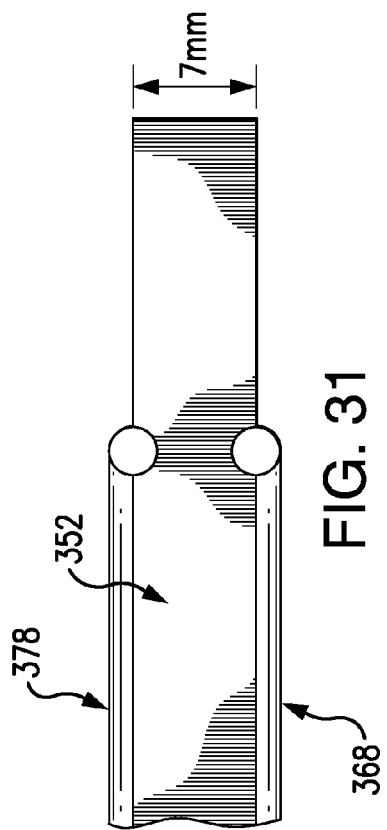

SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Synthetic Construct

<400> SEQUENCE: 1

-continued

```
gttttcccag tc                                                      12

<210> SEQ ID NO 2
<211> LENGTH: 12
<212> TYPE: DNA
<213> ORGANISM: Artificial Sequence
<220> FEATURE:
<223> OTHER INFORMATION: Synthetic Construct

<400> SEQUENCE: 2
caggaaacag ct                                                      12
```

METHODS AND DEVICES FOR ELECTROMAGNETIC AMPLIFICATION OF NUCLEIC ACIDS

CROSS-REFERENCE TO RELATED APPLICATION

This application claims the priority benefit of U.S. Provisional Patent Application No. 61/676,358 filed Jul. 27, 2012, which is hereby incorporated herein by reference.

BACKGROUND

Rapid and cost-effective detection and amplification of nucleic acid is vital for the identification of pathogenic and non-pathogenic agents of biomedical, industrial and research applications as well as other uses in molecular biology and biotechnology. Existing PCR technology, which is typically used in the amplification of DNA, is based on the polymerase chain reaction. Conventionally, a test tube system for DNA replication allows a "target" DNA sequence to be selectively amplified or enriched several-fold in several hours. During such conventional PCR, high temperature is used to separate the DNA molecules into single strands (typically in one to several minutes at 94-96° C.), and synthetic sequences of single-stranded DNA (typically 20-30 nucleotides) serve as primers. Typically, two different primer sequences are used to bracket the target region to be amplified. The primer anneals to the DNA by way of hydrogen bonds. This annealing step typically occurs over about one to several minutes at about 50-65° C. After primer hybridization, the DNA is heated from typically about one to several minutes at about 72° C. in the presence of a polymerase, during which time the polymerase binds and extends a complementary DNA strand from each primer.

Since PCR was first conceived, all known techniques and equipment have required heating elements and temperature controls to thermally treat DNA in each step of the process. However, such techniques and equipment require considerable operating time and heating temperatures, which lead to DNA loss or damage, potential increases of error, and considerable operating and maintenance time and cost. Accordingly, it can be seen that needs exist for improvements in PCR techniques and equipment. The methods and devices described herein address these needs.

SUMMARY

Described herein are methods and devices for amplifying nucleic acids. The methods and devices generally involve exposing the nucleic acid to an electromagnetic field, for example a mini-current electromagnetic field, while performing the steps of PCR. The methods and devices provide numerous advantages over conventional PCR techniques and systems such as reduced reaction times, no heating requirements, and reduced amounts of reagents (e.g., optional use polymerases and primers). Additionally, the methods and devices described herein require significantly shorter reaction times (e.g., less than one hour) compared to conventional PCR techniques and systems (minimum 2 hours). Finally, as shown in the Examples below, the methods and devices described herein amplify significantly more DNA compared to conventional PCR techniques and systems. In summary, the methods and devices described herein provide a more efficient and cost-effective way to perform PCR when compared to conventional PCR techniques and systems.

The advantages described above and below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 12A-12F are bottom-side plan views of vial-support plates with magnetic-field-inducing circuits of the amplification device according to additional alternative embodiments.

FIG. 29 is a top perspective view of the magnetic-field-inducing circuit of the device of FIG. 21.

FIG. 30 is a bottom perspective view of a portion of the magnetic-field-inducing circuit of FIG. 29.

FIG. 31 is a side view of a portion of the magnetic-field-inducing circuit of FIG. 29.

FIG. 32 is a top perspective view of the magnetic-field-inducing circuit of FIG. 29.

DETAILED DESCRIPTION

Figure 1:
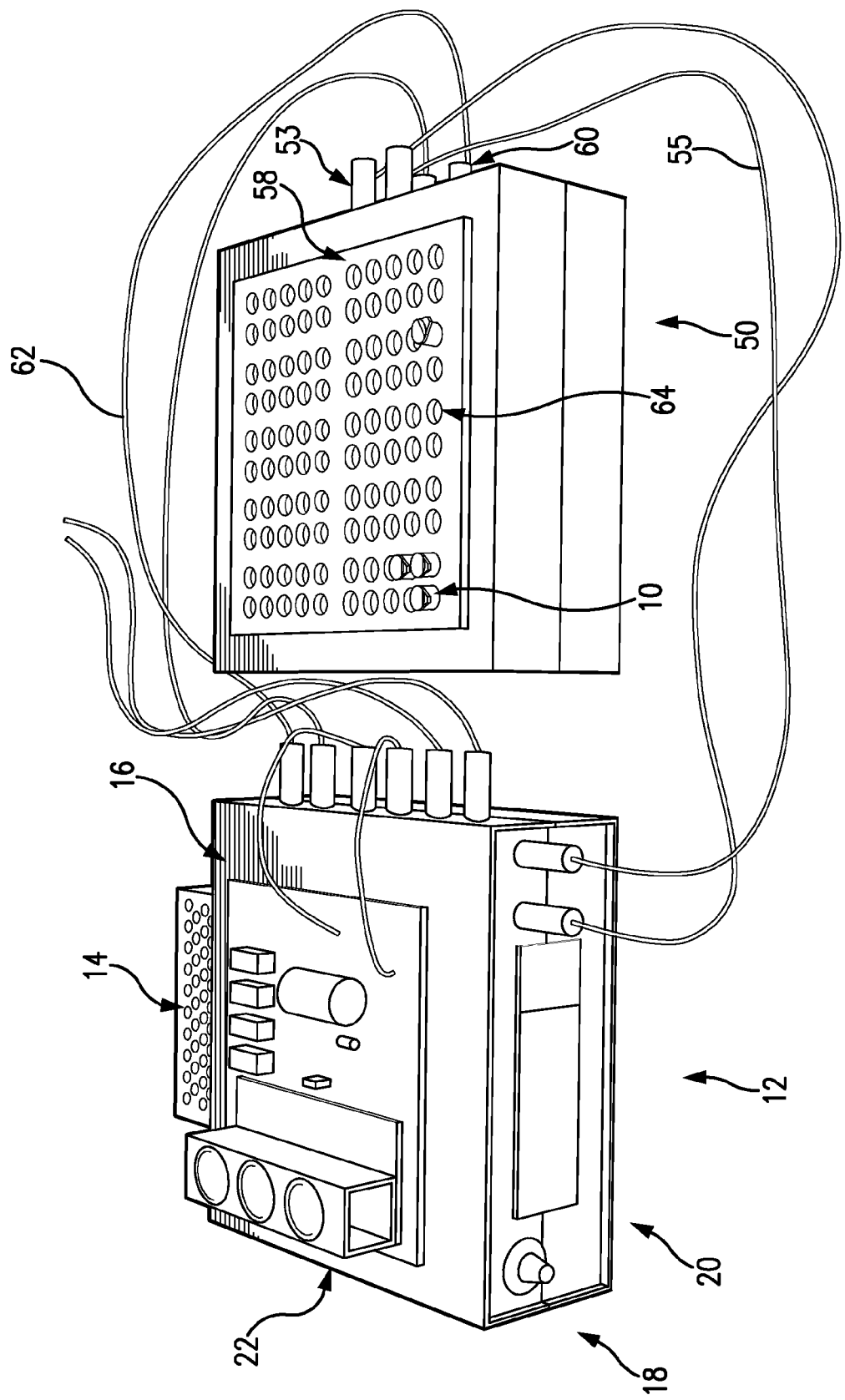
FIG. 1 is a top perspective view of a device for amplifying nucleic acid according to a first example embodiment of the present invention, showing the device holding vials containing the nucleic acid and operably connected to a control unit.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

The singular forms "a," "an" and "the" include plural referents unless the context clearly dictates otherwise. Thus, for example, reference to "a bioactive agent" includes mixtures of two or more such agents, and the like.

Ranges may be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "mini-current" when used in reference to magnetic fields means that the current through the magnetic-field-inducing circuit is sufficiently small in magnitude that the PCR amplification process is substantially thermal-free but sufficiently large in magnitude that a magnetic field is induced that drives the PCR amplification process as intended.

The term "thermal-free" when used in reference to PCR devices and methods means that any heat generated by the magnetic-field-inducing circuit is so small in magnitude and/or is generated so far a distance away from the nucleic acid being processed that it has substantially no material impact on the PCR amplification process. For example, a temperature difference (e.g., between the nucleic acid being processed and a mini-current conductor uniformly positioned relative to each other and uniformly spaced apart by about 0.35 cm at their nearest points) during the PCR process of as much as about 3.7° C., which during testing has been shown to not materially impact the PCR process, is considered to be thermal-free. And in one embodiment, the nucleic acid is amplified in the PCR device from 25° C. to 30° C., which during testing has been shown to not materially impact the PCR process, and is considered to be thermal-free. Thus, "thermal-free" does not mean that absolutely no heat is generated or that the nucleic acid being processed is subjected to absolutely no heat; rather, it means that any such heat has no more than a negligible effect on the quantity and quality of the resultant amplified nucleic acid.

I. Devices

Described herein are devices for amplifying a nucleic acid. The devices are operable to induce a mini-current magnetic field and subject nucleic acid to the magnetic field to thereby amplify the nucleic acid by a PCR process. The PCR device of typical embodiments amplifies the nucleic acid by the application of the magnetic field, not by applying heat, so the process is thermal-free. The PCR device of other embodiments amplifies the nucleic acid by the application of the magnetic field and also by applying heat (e.g., from heating elements), for a combination of a magnetic-field process and a thermal process. The result is that the desired amplification can be accomplished in significantly reduced time.

Turning now to the drawings, FIGS. 1-11 show a device 50 for amplifying a nucleic acid 50 according to a first example embodiment of the present invention. The amplification device 50 is a used with a control unit 12 and vials 10 of nucleic acid samples such as those depicted.

Figure 2:
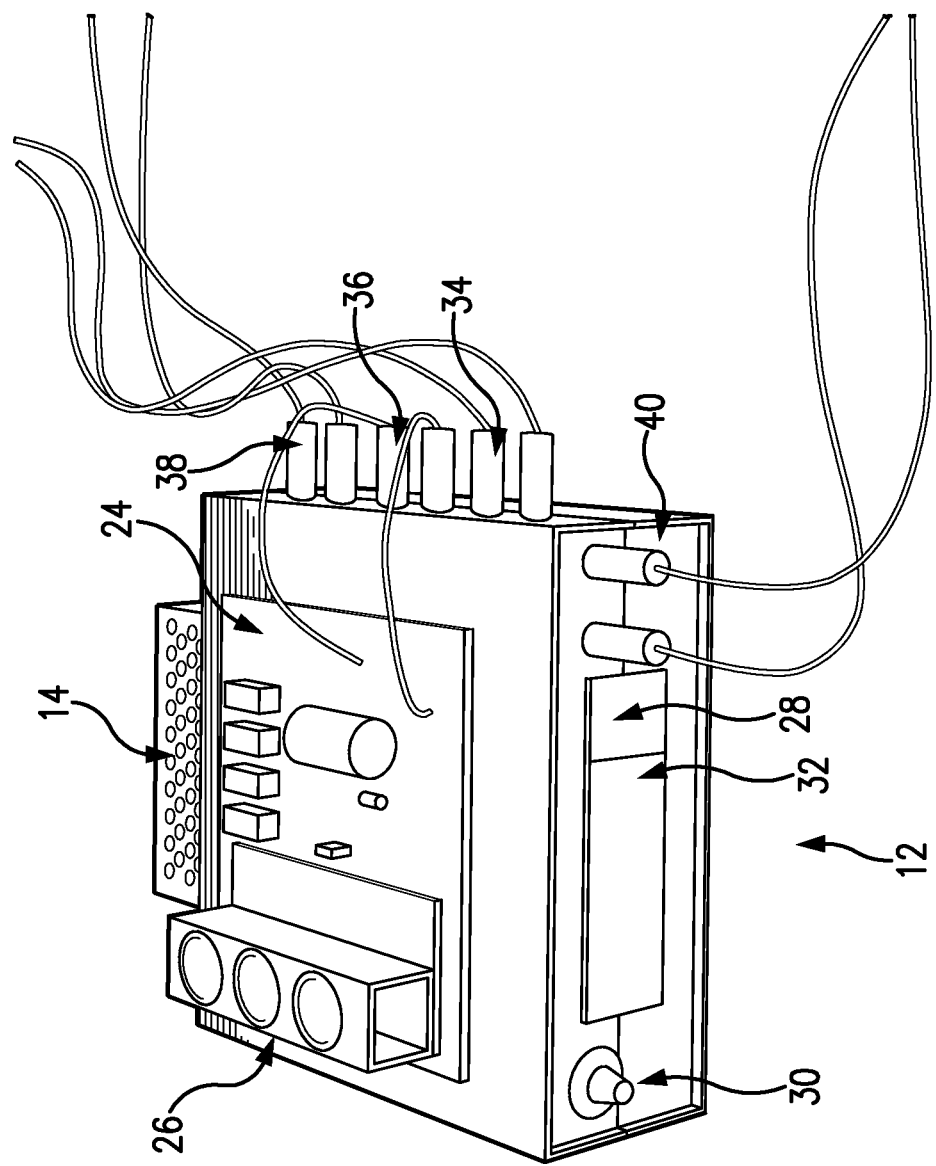
FIG. 2 is a top perspective view of the amplification device of FIG. 1.
Figure 7:
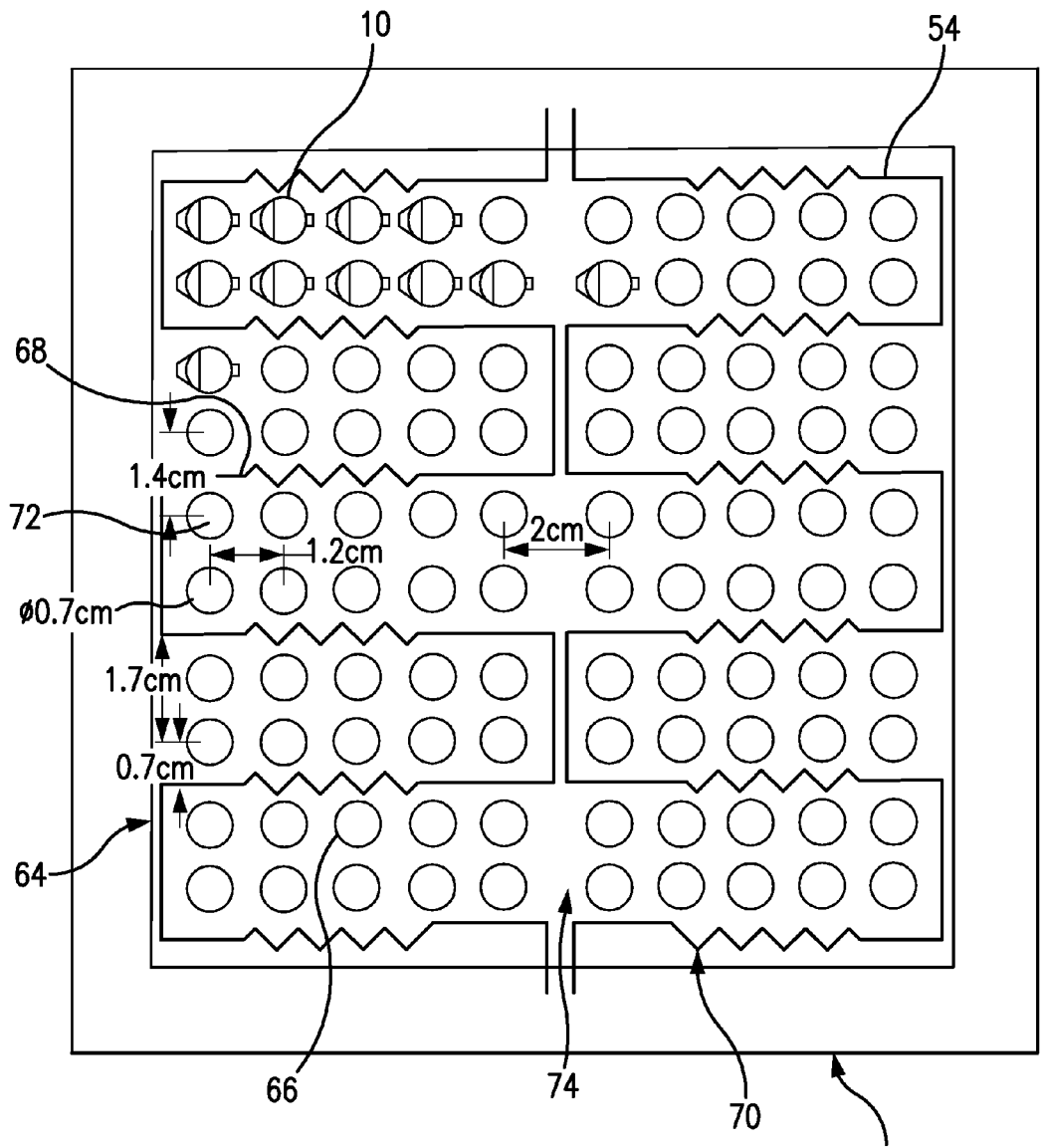
FIG. 7 is a top plan view the amplification device of FIG. 1.
Figure 7A:
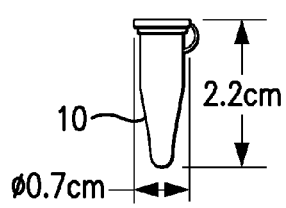
FIG. 7A is a side plan view of an example one of the vials used with the amplification device of FIG. 1.

Referring with particularity to FIGS. 1-2 and FIG. 7A, the vials 10 can be of conventional types, made of conventional materials, and provided in standard sizes, and are sometimes synonymously referred to as tubes. For example, the vials 10 typically have volumes of 0.2 mL, 0.6 mL, 1.0 mL, 1.5 mL or 2.0 mL. The wall thickness of the sample vials 10 can be selected in order to maximize magnetic field distribution. For example, the vials 10 typically have sidewall thicknesses of 0.5 mm to 1.5 mm, preferably 1.15 mm to 1.20 mm, and more preferably 1.17 mm. It will be understood that the term "vial" is used herein broadly to include any container capable of holding nucleic acid samples for processing by any of the amplification devices described herein and similar devices. In embodiments in which the vials are not tubular, corresponding modifications can be made to a support for the vials.

The control unit 12 can be of a conventional type known in the art, such as those commercially available from MCP (Shanghai MCP Corp. of Shanghai, China) including programmable power supply model M10-SPP1203. The control unit 12 includes a power supply 14, control circuitry and/or a programmed processor 16, one or more control inputs 18, and one or more control outputs 20, all assembled into a control housing 22. The power supply 12 can include transformers for stepping down delivered voltages (typically 110V) to the operating voltage of the PCR device 30, which in typical commercial embodiments is 12V. Alternatively, the power supply 12 can provide other operating voltages and/or include conventional batteries. The control circuitry and/or programmed processor 16 can include a source power card management system 24 with power transistors 26, as depicted, designed to control the power delivered to the PCR device. Alternatively, the control circuitry and/or programmed processor 16 can include other conventional control systems as are well known in the art. The control inputs 18 can include a keyboard 28 and knob 30, as depicted, and/or another conventional input such as a touchscreen or pushbuttons. The control outputs 20 can include a display screen 32, as depicted, and/or another conventional output such as an alarm sound or light generator. And the control housing 22 is sized to house (internally and/or externally) all these components and typically made of a metal or other appropriately strong and durable material. In addition, the control unit 12 can include input connectors 34 for the input power, output connectors 36 for connection to the power supply 14, output connectors 38 for connection to cooling system input connectors 60 of the PCR device 50, and output connectors 40 for connection to power input connector 53 of the PCR device. As such, the control system 12 of the depicted and other typical embodiments can be made of conventional components selected, configured, and interconnected by a person of ordinary skill in the art to produce the functionality described herein.

Figure 3:
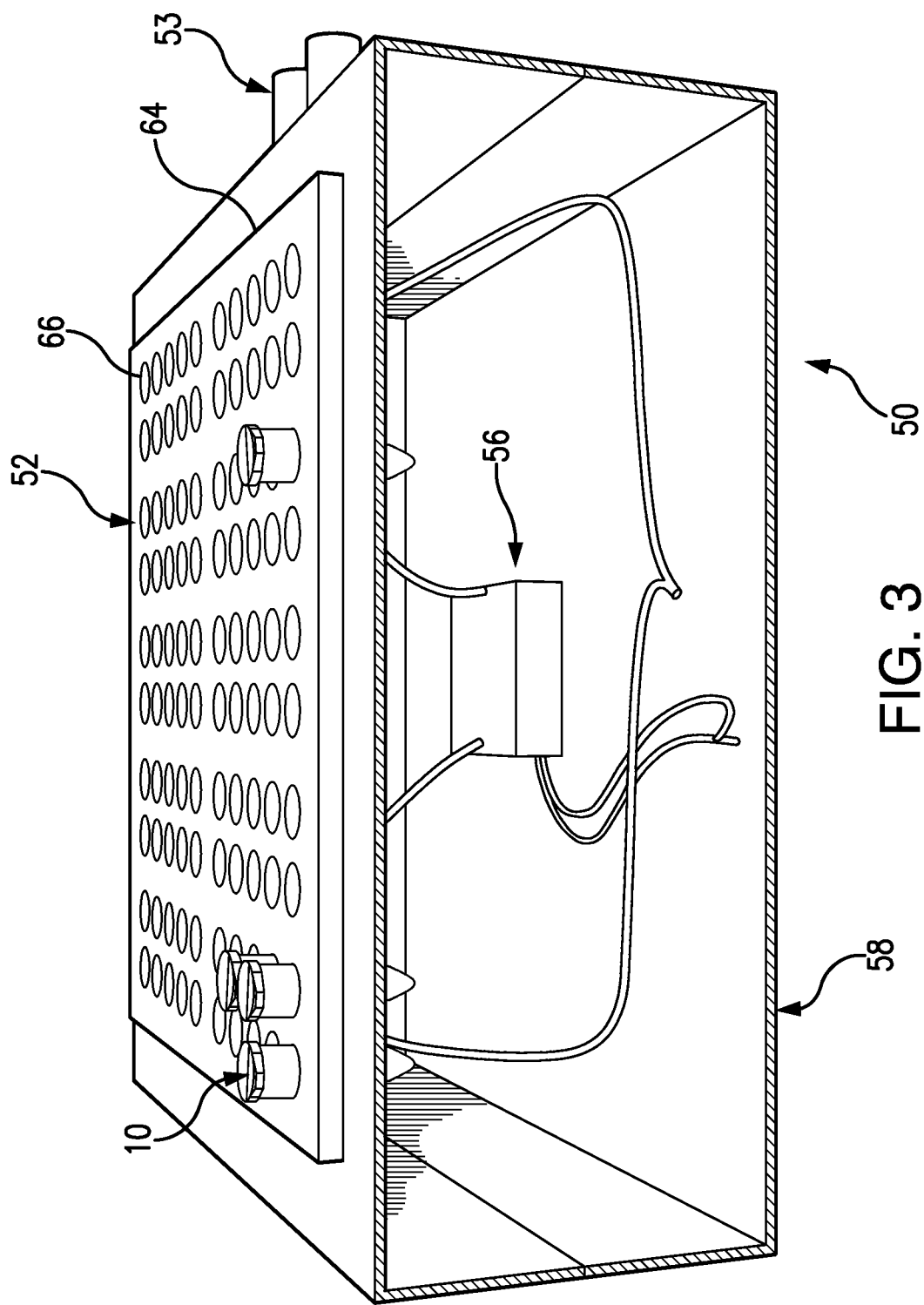
FIG. 3 is a top perspective view of the amplification device of FIG. 2, with the front panel of its housing removed to show the internal components.
Figure 4:
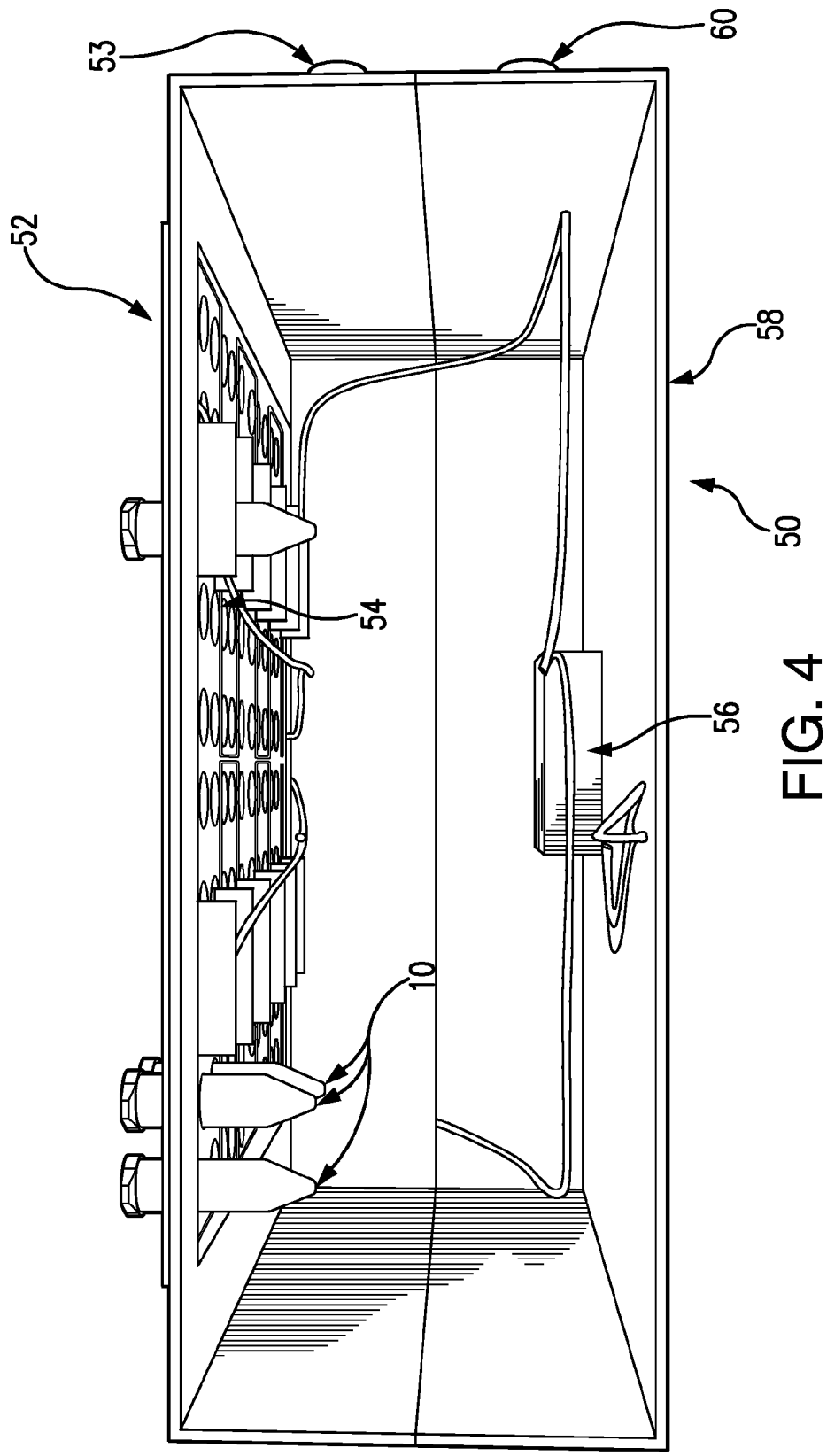
FIG. 4 is a front perspective view of the amplification device of FIG. 3.
Figure 5:
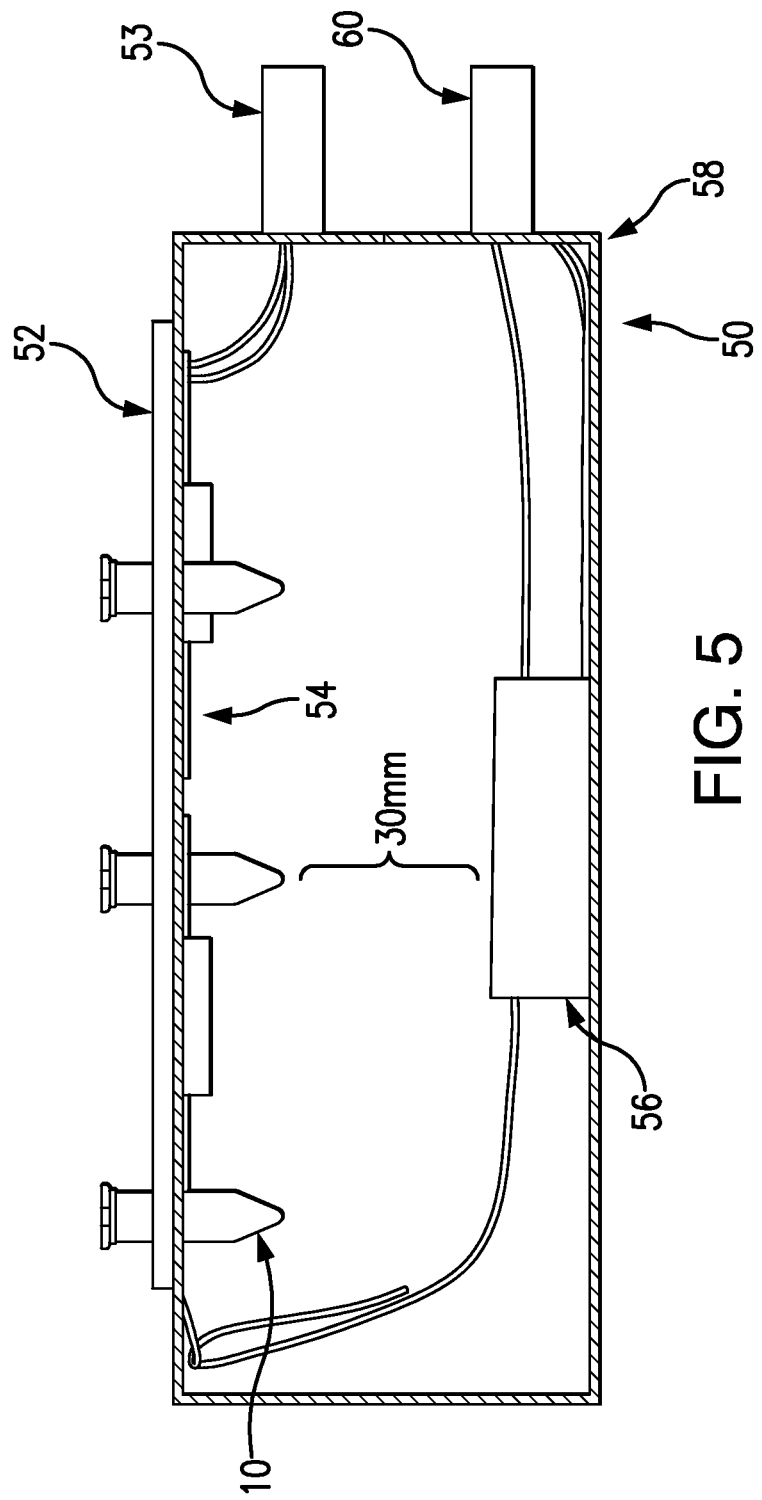
FIG. 5 is a front view of the amplification device of FIG. 3.
Figure 6:
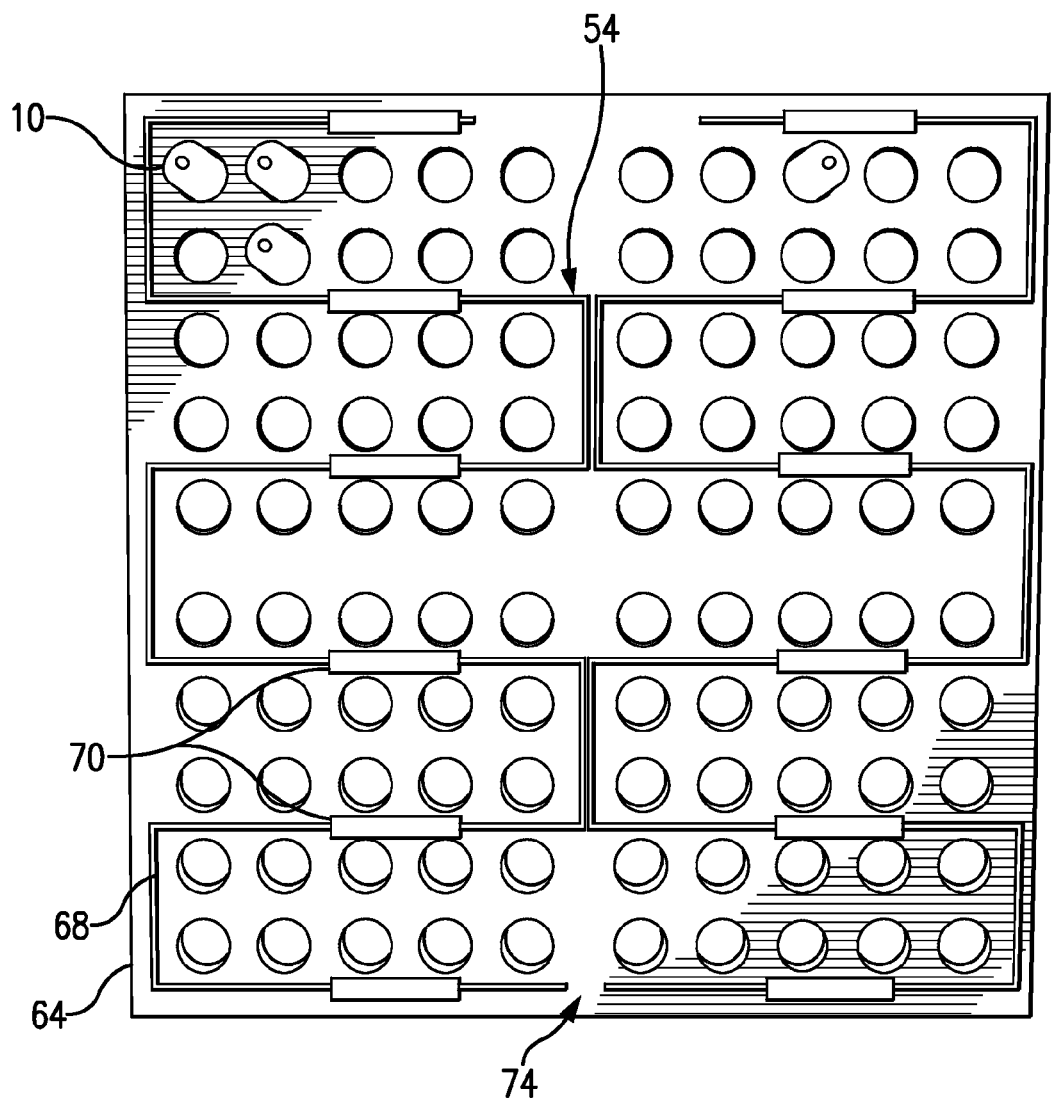
FIG. 6 is a bottom-side plan view of a vial-support plate with a magnetic-field-inducing circuit of the amplification device of FIG. 1.

Referring now with particularity to FIGS. 3-5, the PCR amplification device 50 includes a vial support 52 and a circuit 54 that induces an electromagnetic field. In addition, the PCR amplification device 50 typically includes a cooling system 56 as well as a housing 58 for all of these components.

The housing 58 can be composed of any material selected for sufficient strength and durability including, but not limited to, low-density polyethylene, another plastic, rubber, glass, mixed glass (e.g., such as that sold under the PLEXIGLAS brand), acrylic, polycarbonate, and composite thereof. In some embodiments the housing 58 is not included and instead the vial support 52 includes legs or other base structures for elevating and providing clearance for the vials 10 held by it. And in other embodiments, the housing 58 is provided by a structure that elevates and provides clearance for the vials 10 but does not actually house or enclose any components, and instead is open to allow any heat generated by the process to escape more freely and not materially impact the thermal-free PCR process. For example, the housing 58 can be in the form of an open or lattice frame, an X- or H-frame, or simply four support legs or two opposing support panels extending downward from the vial support 52. In some embodiments such as that depicted, the housing 58 includes a bottom wall and a peripheral sidewall (e.g., made of four sidewall panels), with a top wall formed at least in part by the vial support 52. In embodiments such as this, the housing 58 does not enclose or circumscribe the vials 10 in their entirety, only their portions below the vial support 52. In typical embodiments, power input connectors 53 are provided for connection to power output connectors 40 of the control unit 12 by power wires 55 (see FIG. 1).

The cooling system 56 typically includes a conventional cooling fan positioned for example generally centrally within the housing 58. The fan 56 can be of a conventional type known in the art, such as that commercially available from Cooler Master Co., Ltd. (Chung Ho City, Taiwan) under the SICKLEFLOW brand. The fan 56 is wired to cooling system input connectors 60 on the housing 58, which connectors provide for connection to output connectors 38 of the control unit 12 by fan wires 62 for power and control (see FIGS. 1-2). In use, the cooling system 56 can be set at a desired temperature (e.g., 25° C. to 26° C.) so that it will automatically turn on and off to maintain the pre-set constant temperature in the housing 58 for the duration of the PCR process. As such, the cooling system 56 can include automatic controls including conventional temperature sensors such thermocouples.

In some embodiments, the cooling system 56 is not provided because the magnetic-field-inducing circuit 54 generates such little heat that the samples in the vials 10 are not heated by it at all (or at least they're heated so little that this has no material impact on the PCR process). And the motor of the fan 56 generates such little heat that the samples in the vials 10 are not heated by it at all (or at least they're heated so little that this has no material impact on the PCR process). To ensure this thermal-free operation, the fan 56 can be spaced apart from the vials 10 far enough that any heat from the fan motor does not reach the vials but close enough that the fan still moves air across the vials. In the depicted embodiment, for example, the fan is spaced about 30 mm from the circuit 54.

The vial support 52 typically includes a plate 64 with an array of holes 66 formed in it. In the depicted embodiment, the holes 66 are circular with an about 0.7 cm diameter for holding vials 10 with a 0.7 cm diameter. The holes 66 are typically spaced uniformly in each direction so that the magnetic field generated by the circuit 54 is uniformly applied to all of the vials. In the depicted embodiment, the vial-support plate 64 includes 100 of the holes 66 in a 10×10 array, though more or fewer holes can be provided for any application as may be desired. The vial-support plate 64 can be made of any material selected for sufficient strength and durability including, but not limited to, Bakelite, another plastic, carbon-fiber materials, and composites thereof. In other embodiments, instead of a plate, the vial support 52 is provided by a frame such as a lattice, an array of hooks, eyes/loops, or other suspension elements, or another structure that defines an array of openings for the vials and supports them in position. And in embodiments in which the vials 10 are not tubular, the vial support 52 can be modified accordingly so that the holes 66 have a shape for holding the vials in place. As such, the holes 66 can be other than circumferential openings and instead can be provided by notches, slots, or other openings.

Referring now with particularity to FIGS. 4-9, the magnetic-field-inducing circuit 54 includes at least one conductor 68 through which a min-current I is passed to induce a magnetic field B. In typical embodiments, the conductor 68 is provided by a copper wire, though other conductive materials can be used. The conductor 68 has terminals that are electrically connected for example by wiring to the power input connectors 53 on the housing 58, which connectors provide for connection to power output connectors 40 of the control unit 12 by power wires 55 for power and control (see FIGS. 1-2).

For typical commercial embodiments, examples of the approximate voltage of and mini-current I through the circuit 54, and the magnetic field B induced by the circuit 54 and applied to the samples, are shown in Tables 1 and 2. Each of the ranges between each of the listed approximate values is considered to represent a separate embodiment and mode of use. Note that the magnetic field B is the strength of the magnetic field at and applied to the samples in the vials 10, which is necessarily less than the core magnetic field immediately adjacent the conductor 68 inducing it due to the distance spacing "d" between the conductor and the vial centers. And note that the distance d refers to the conductor-to-vial-centerline spacing, however, this spacing and the conductor-to-sample spacing (where an outer-most portion of the sample is first exposed to the effect of the magnetic field) in some embodiments can be considered to be substantially the same due to the relatively small diameter of the vials 10 and the fluid dynamics of the samples in the vials. In other embodiments, however, the diameter of the vials 10 (or tubes or other sample-holding containers) relative to the vial-centerline spacing from the magnetic-field-inducing conductor 68 is relatively large, and the samples in the vials have relative fluid dynamics, such that the induced magnetic field is adjusted to account for the fact that certain portions of the samples in the vials are much closer to the conductor.

In Table 1, the voltage and current I were varied to produce various magnetic fields B on the samples to assess the resulting amplification. And in Table 2, the voltage and resistance were varied to produce the same current I and magnetic field B on the samples to assess different design and construction options. In both Tables, the distance "d" is 7 mm.

TABLE 1

| Working Voltage (VDC) | Mini-Current I (Amps) | Magnetic Field B (Gauss) |
|---|---|---|
| 0.01 | 0.005 | 0.001 |
| 0.05 | 0.025 | 0.009 |
| 0.1 | 0.05 | 0.019 |
| 0.2 | 0.10 | 0.039 |
| 0.3 | 0.15 | 0.059 |
| 0.4 | 0.20 | 0.080 |
| 0.5 | 0.25 | 0.100 |
| 0.6 | 0.30 | 0.120 |
| 0.7 | 0.35 | 0.141 |
| 0.8 | 0.40 | 0.161 |
| 0.9 | 0.45 | 0.180 |
| 1.0 | 0.50 | 0.200 |
| 1.2 | 0.60 | 0.241 |
| 1.4 | 0.70 | 0.282 |
| 1.5 | 0.80 | 0.322 |
| 1.8 | 0.90 | 0.360 |
| 2.0 | 0.90 | 0.360 |
| 2.0 | 1.00 | 0.402 |

TABLE 2

| Working Voltage (VDC) | Mini-Current I (Amps) | Resistance (Ohms) | Magnetic Field B (Gauss) |
|---|---|---|---|
| 0.5 | 0.9 | 0.56 | 0.36 |
| 1.0 | 0.9 | 1.11 | 0.36 |
| 1.5 | 0.9 | 1.67 | 0.36 |
| 2.0 | 0.9 | 2.22 | 0.36 |
| 2.5 | 0.9 | 2.78 | 0.36 |
| 3.0 | 0.9 | 3.33 | 0.36 |
| 3.5 | 0.9 | 3.89 | 0.36 |
| 4.0 | 0.9 | 4.44 | 0.36 |
| 4.5 | 0.9 | 5.0 | 0.36 |
| 5.0 | 0.9 | 5.56 | 0.36 |
| 5.5 | 0.9 | 6.11 | 0.36 |
| 6.0 | 0.9 | 6.67 | 0.36 |
| 6.5 | 0.9 | 7.22 | 0.36 |
| 7.0 | 0.9 | 7.78 | 0.36 |
| 7.5 | 0.9 | 8.33 | 0.36 |
| 8.0 | 0.9 | 8.89 | 0.36 |
| 8.5 | 0.9 | 9.44 | 0.36 |
| 9.0 | 0.9 | 10.0 | 0.36 |
| 9.5 | 0.9 | 10.56 | 0.36 |
| 10.0 | 0.9 | 11.11 | 0.36 |
| 10.5 | 0.9 | 11.67 | 0.36 |
| 11.0 | 0.9 | 12.22 | 0.36 |
| 11.5 | 0.9 | 12.78 | 0.36 |
| 12.0 | 0.9 | 13.33 | 0.36 |

In a preferred embodiment, the PCR device 50 is operated with good results at about 12V with a mini-current I of about 900 mA to induce a magnetic field B of about 0.35 to about 0.36 Gauss on the nucleic acid samples in the vials 10 holding them when the vials and the magnetic-field-inducing conductor 68 are uniformly positioned relative to each other and uniformly spaced apart by a distance d of, for example, about 0.7 cm (e.g., about 0.35 cm at their closest points for vials with a diameter of about 0.7 cm). In other preferred embodiments, the PCR device 50 is operated with a mini-current I of about 800 mA to induce a magnetic field B of about 0.322 Gauss on the samples, with a mini-current I of about 1.0 A to induce a magnetic field B of about 0.402 Gauss on the samples, or with a mini-current I and a magnetic field B within the ranges defined by those approximate values.

It will be understood that the PCR device 50 can be operated to induce a magnetic field B of higher or lower strengths on the samples to produce the intended results as described herein. In some embodiments, for example, the magnetic-field-inducing conductor 68 is spaced a different distance d (than the 0.7 cm spacing of the depicted embodiment) from the centerlines of the vials 10 holding the samples, and/or a current I of a different strength is passed through the conductor 68 (by using a different voltage and/or resistance), so that a magnetic field B of different strength is induced by the conductor and applied to the samples. Typically, for a decreased distance d and/or a stronger current I, a stronger magnetic field B is induced, and for an increased conductor-to-sample spacing and/or a weaker current, a weaker magnetic field is induced, to produce the desired amplification.

In other embodiments, a core magnetic field of a different strength is induced to apply the same-effect magnetic field B to the samples. For example, in some embodiments the magnetic-field-inducing conductor 68 is spaced a different distance d (than the 0.7 cm spacing of the depicted embodiment) from the vials 10 holding the samples, so a current I of a different strength is passed through the conductor 68 (by using a different voltage and/or resistance) in order to induce a core magnetic field of a different strength such that, given the different conductor-to-sample spacing, the magnetic field B at and applied to the samples is still in the same range of about 0.322 Gauss to about 0.402 Gauss. And in other embodiments, a current I of a different strength is passed through the conductor 68, so a core magnetic field of a different strength is induced, and in order for the magnetic field B at and applied to the samples to be still in the same preferred range of about 0.322 Gauss to about 0.402 Gauss, a different conductor-to-sample distance spacing d is used.

In order to determine the conductor-to-vial distance spacing d and the current I to provide a magnetic field B at and applied to the samples in for example the preferred range of about 0.322 Gauss to about 0.402 Gauss, the following formula (known as the "Biot and Savat" equation) is used:

$$B = \frac{Mo * I}{2\pi * d}$$

in which "Mo" is the magnetic permeability in empty space, a constant of $4\pi \times 10^{-7}$ and in which d and I are as defined herein. In embodiments such as this in which each sample in each vial 10 is affected by magnetic fields from two sides (see FIGS. 8-9), the magnetic fields can be calculated separately and then added together.

The magnetic-field-inducing circuit 54 typically includes a plurality of resistors 70 to set the voltage. The rating of the resistors 70 is selected to maintain the voltage at the desired pre-set level; a person of ordinary skill in the art can properly select the resistor ratings. The resistors 70 can be made of a carbon material with a low concentration of copper (for example, with a carbon-to-copper ratio of 80/20, 90/10, or 95/5), copper fiber, ferronickel, or other electric-resistive materials known in the art. In a typical commercial embodiment with a 10×10 array of holes 66 and the conductor 68 routed adjacent to and uniformly positioned relative to all of the holes and uniformly spaced apart about 0.35 cm at their closest points, the resistors 70 can have a resistance of about 1 ohm to about 5 ohms, with a resistance of about 1.5 ohms working well. This resistance is sufficiently small in magnitude that very little heat is generated by the mini-current I flowing through the resistors 70 such that the PCR process remains thermal-free. And to ensure that any heat from the resistors 70 does not materially impact the PCR process, the cooling system 56 can be operated to dissipate such heat.

In the depicted embodiment, the magnetic field B is induced simply by running the mini-current I through the conductor 68 of the circuit 54. In other embodiments, the circuit includes coiled wires to induce a concentrated magnetic field of a greater magnitude. And in still other embodiments, there are more or fewer resistors and/or additional circuit components are included, as persons of ordinary skill will understand and be capable of selecting to induce the desired magnetic field while maintaining the process as thermal-free.

Figure 8:
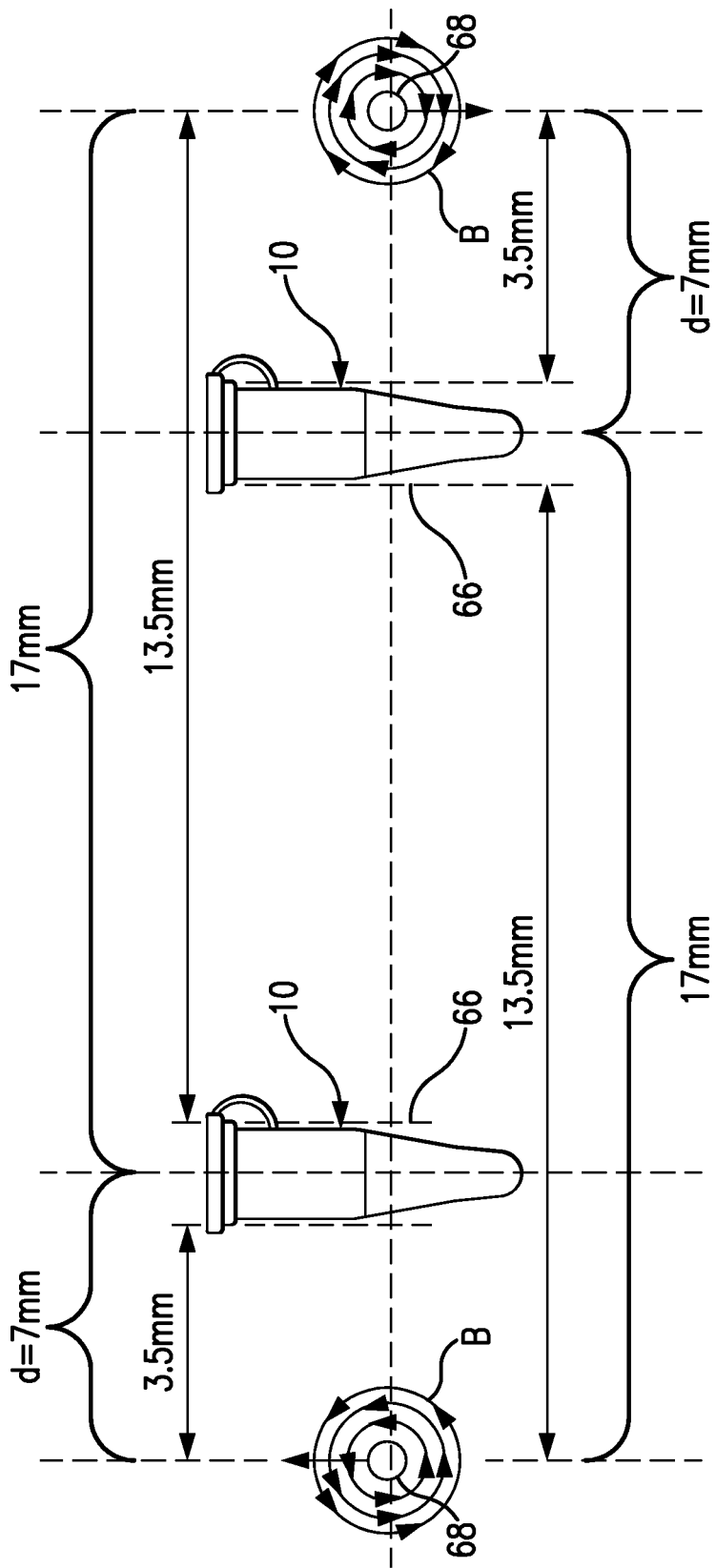
FIG. 8 is a side view depicting the relative positions of the vials held by the vial-support plate and the conductors of the magnetic-field-inducing circuit of the amplification device of FIG. 1.
Figure 9:
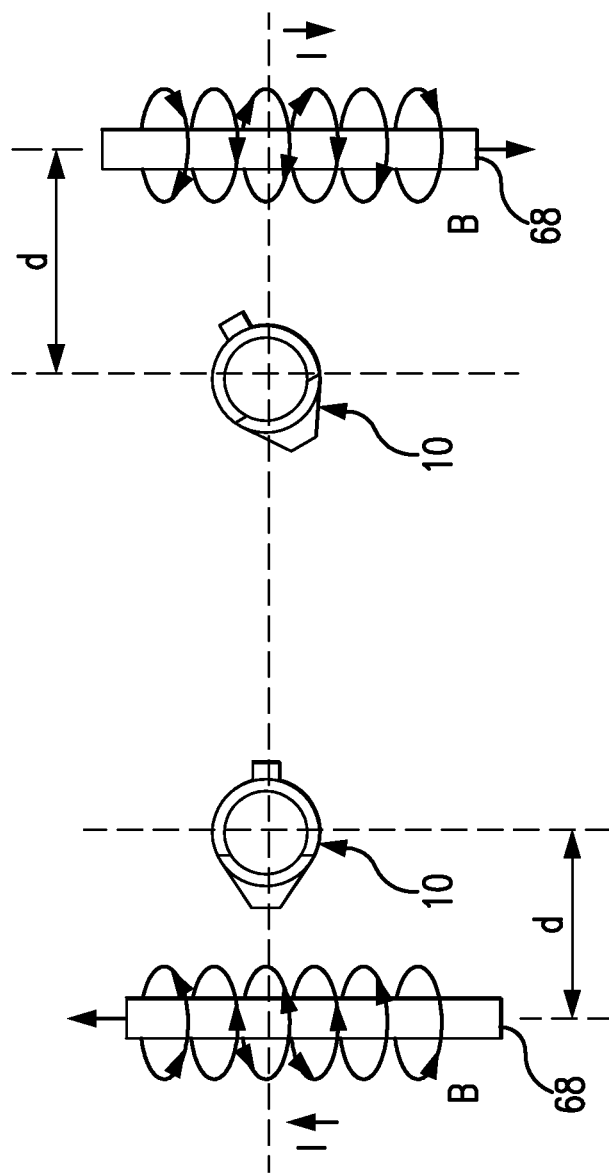
FIG. 9 is a plan view of the depiction of FIG. 8.

The conductor 68 is routed in a position equidistant from all of the holes 66 in the closest row so that each of the vials 10 is the same normal distance away the conductor. In this way, the magnetic field B generated by the circuit 54 is uniformly applied to the samples in all of the vials 10. In particular, the conductor 68 can be routed centrally between every other row of the holes 66 such that the centers 72 of all of the holes are the same normal distance from the conductor. For example, in the depicted embodiment the holes 66 of the vial-support 64 are uniformly spaced apart center-to-center in an array by 1.4 cm in one direction and by 1.2 cm in the perpendicular direction, with the conductor 68 routed midway between each row of the holes whose centers are spaced apart by 1.4 cm. So the conductor 68 is equidistantly positioned 0.7 cm away from the center of each of the holes 66 and equidistantly positioned 0.35 cm away from the holes 66 at the closest point. It should be noted that these and other dimensions shown in FIG. 8 are representative and included for illustration purposes only, and as such are not limiting of the invention.

The circuit 54 is typically mounted to the bottom side of the vial-supporting plate 64, as shown, for ease of manufacture. Alternatively, the circuit 54 can be positioned in another location so long as the magnetic field B is still uniformly applied to and equidistant from all the samples in the vials 10. For example, the conductor 68 can be attached to a mounting board with holes aligned with the holes 66, and the board can be vertically spaced from the vial-support 52 and positioned adjacent the bottoms of the vials to place the magnetic field B closer to the samples in the vials 10 while keeping the conductor 68 equidistant from all the samples in the vials. In other embodiments, the conductor 68 is embedded into or mounted atop the vial support 52. In the depicted embodiment, the conductor 68 is positioned in a plane that is parallel to the vial-supporting plate 64 and perpendicular to the vials 10. In other embodiments, the conductor 68 is positioned in a plane that is not parallel to the vial-supporting plate 64 and not perpendicular to the vials 10. And in other embodiments the circuit 54 includes multiple conductors 68 in multiple planes that are spaced apart from each other, for example, a first conductor in a first plane and a second conductor in a second plane that is spaced apart from the first plane. In the depicted embodiment, the circuit 54 actually includes two circuits. In such embodiments, the two conductors 68 can be routed between the same two holes 66 in some doubled places. To allow for the extra space needed for this while still maintaining the uniform hole-to-conductor spacing, the vial-supporting plate 64 can have a wider spacing area 74 between two rows of holes 66 to accommodate the doubled wire.

Figure 10:
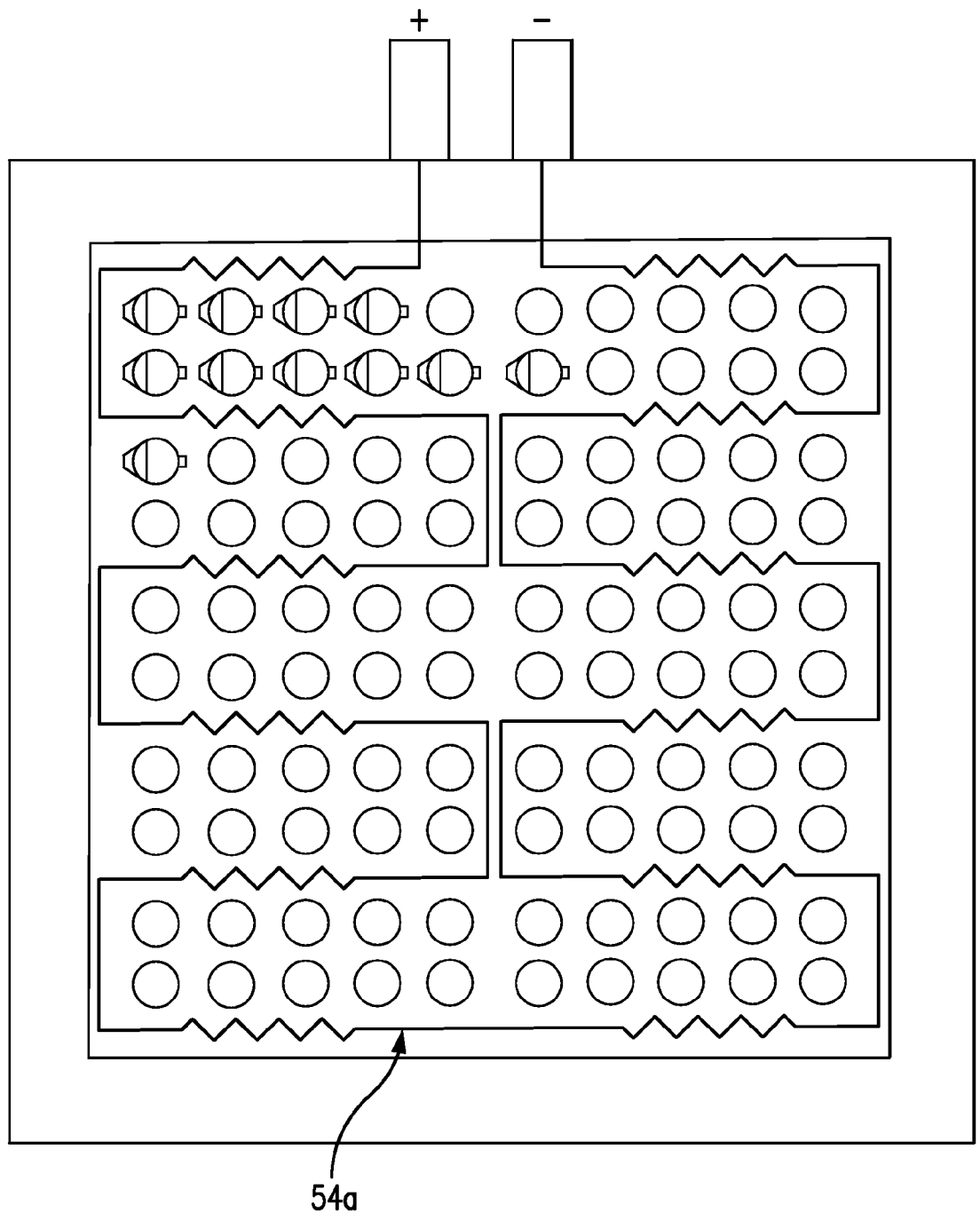
FIG. 10 is a bottom-side plan view of a vial-support plate with a magnetic-field-inducing circuit of the amplification device according to a first alternative embodiment.
Figure 11:
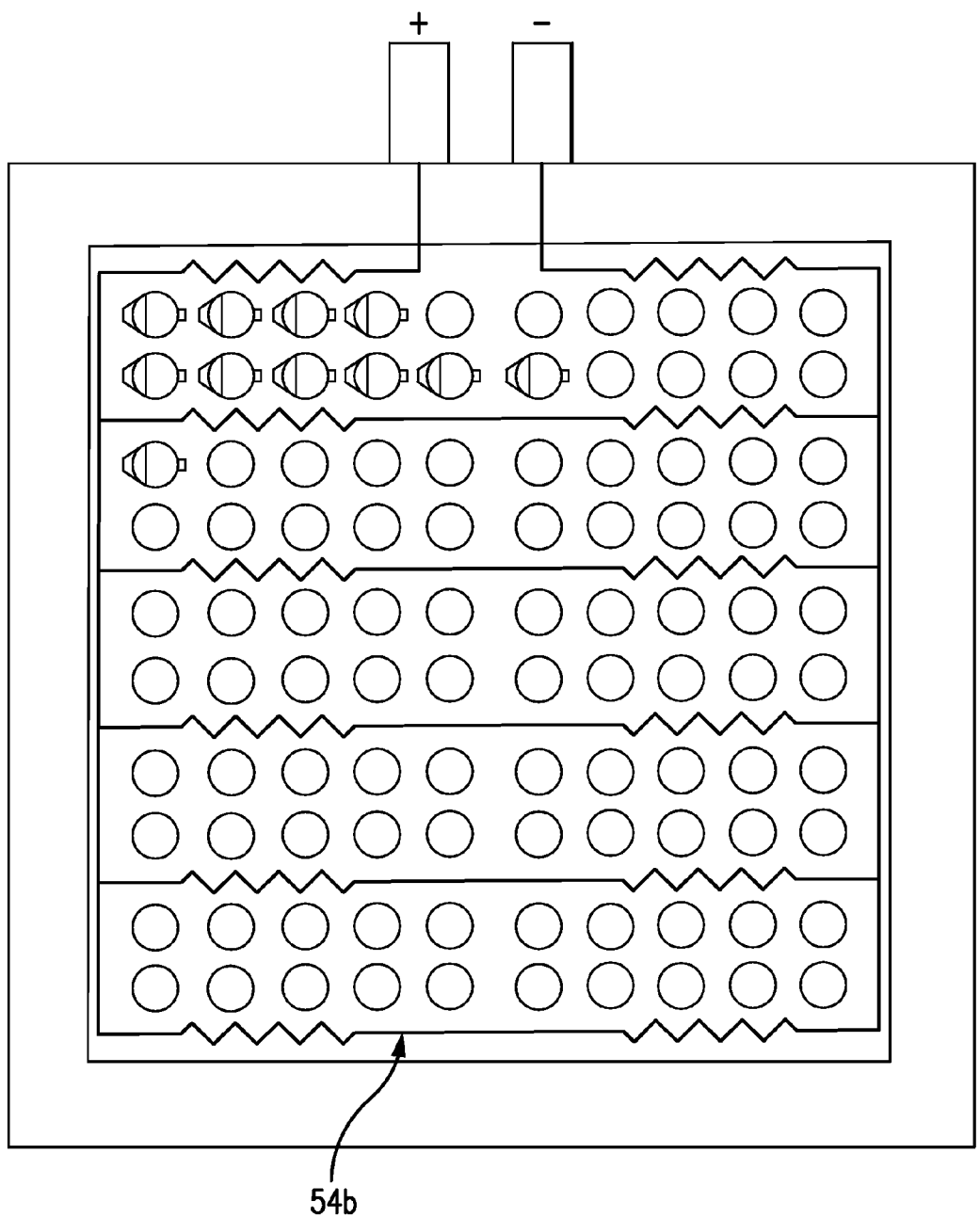
FIG. 11 is a bottom-side plan view of a vial-support plate with a magnetic-field-inducing circuit of the amplification device according to a second alternative embodiment.

The magnetic-field-inducing circuit 54 of this embodiment is a serial circuit (actually, two serial circuits on one vial support 52). The magnetic field can be induced by circuits having other configurations, so long as they induce the desired magnetic field and retain the PCR process as thermal-free. For example, FIG. 10 shows a first alternative circuit 54$a$ that can be used in the device 50 and that is the same as that of FIGS. 6-7 except that the two serial circuits are combined into a single serial circuit. And FIG. 11 shows a second alternative circuit 54$b$ that can be used in the device 50 and that is similar to that of FIG. 10 except that it's a parallel circuit. In other embodiments, the conductor is routed centrally between every row of the holes such that the centers of all of the holes are the same normal distance from the conductor routed on two opposite sides thereof. In yet other embodiments, the circuit includes series and parallel portions, for example, the alternative circuits 54$c$(i)-54$c$(vi) depicted in FIGS. 12A-12F respectively. It will be understood that circuits having many other designs can be included in the device 50.

Figure 13:
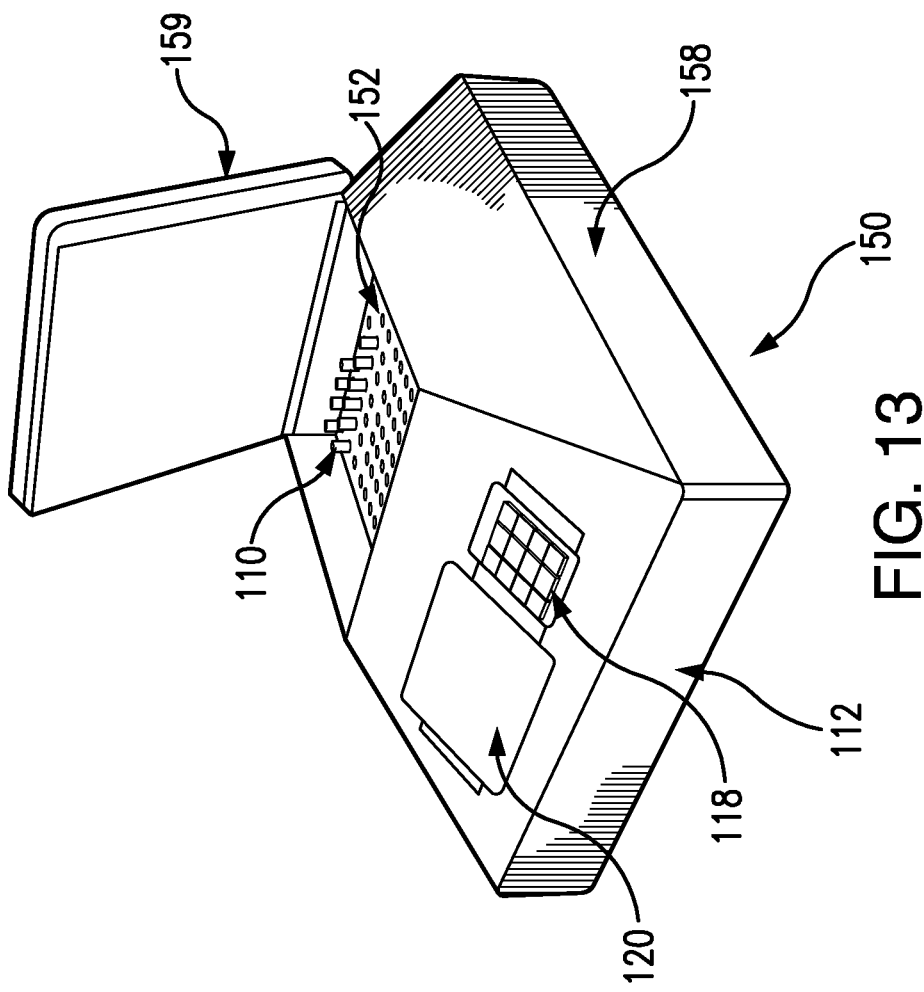
FIG. 13 is a top perspective view of a device for amplifying nucleic acid according to a second example embodiment of the present invention, showing the device holding vials containing the nucleic acid and including an integral control unit.
Figure 14:
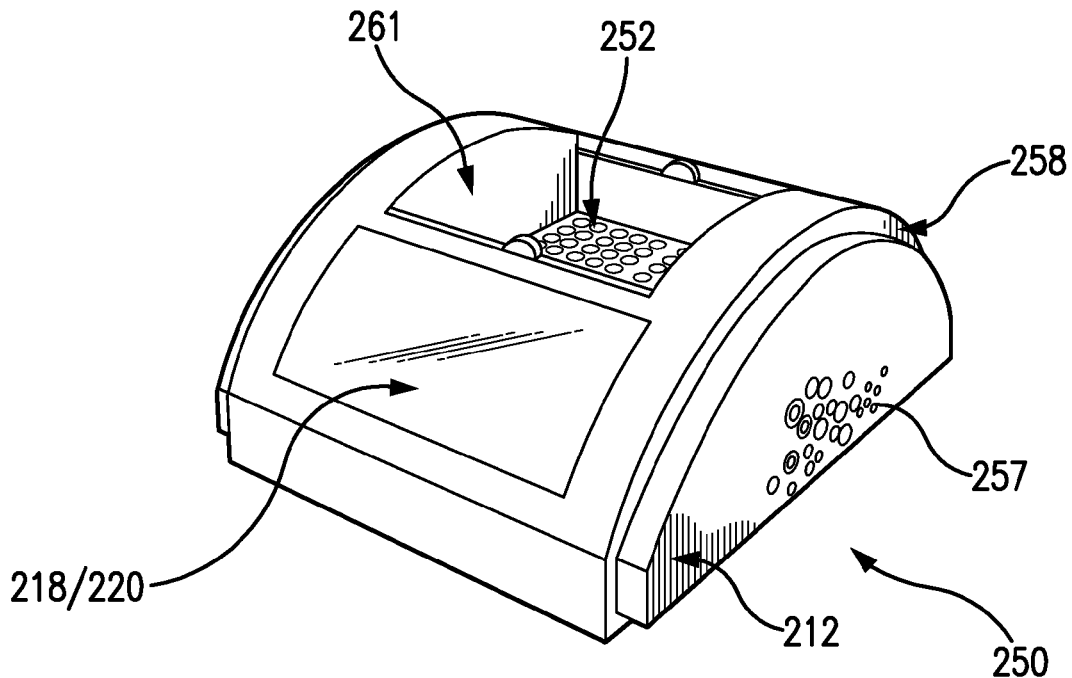
FIG. 14 is a perspective view of a device for amplifying nucleic acid according to a third example embodiment of the present invention, showing the access panels in an open position and an integral control unit.
Figure 15:
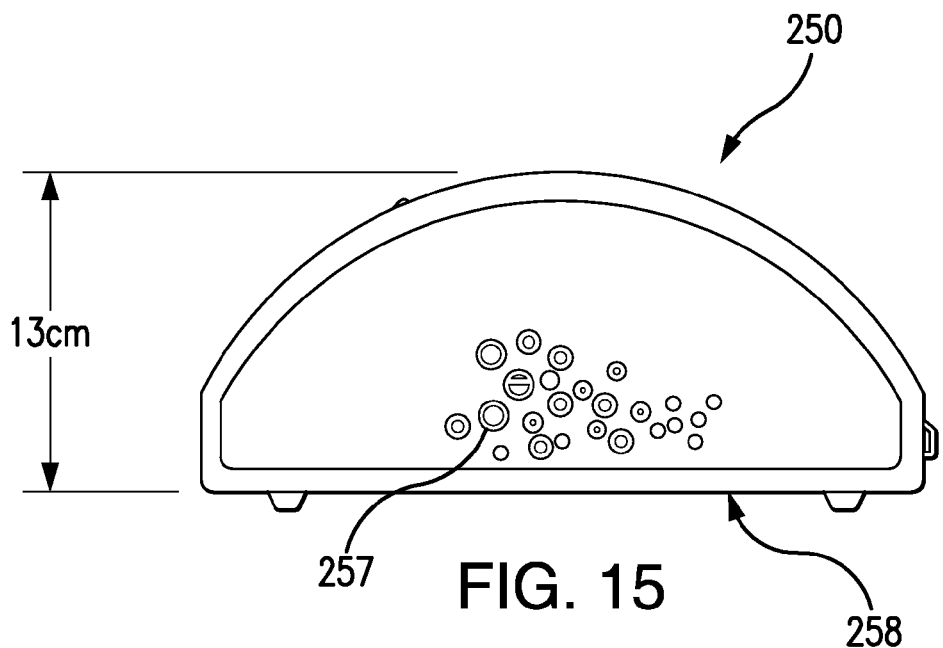
FIG. 15 is a right side view of the device of FIG. 14.
Figure 16:
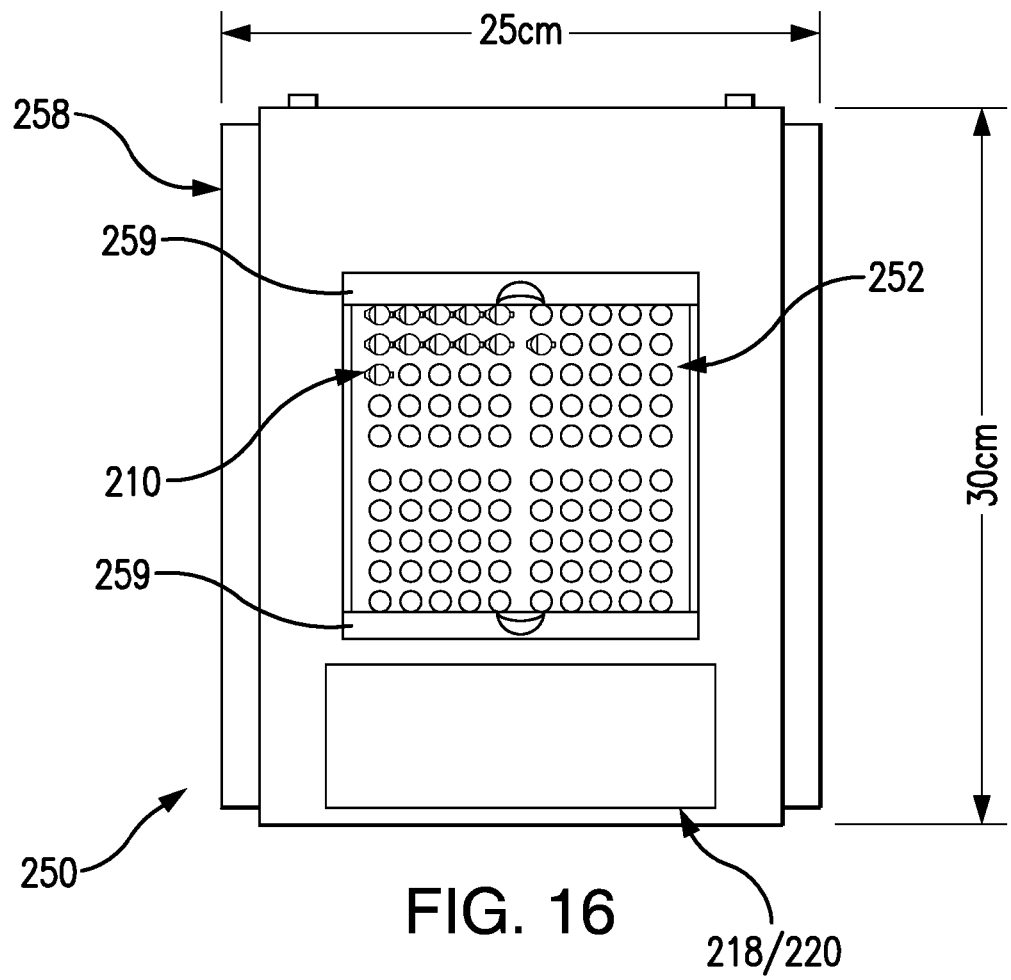
FIG. 16 is a top view of the device of FIG. 14.
Figure 17:
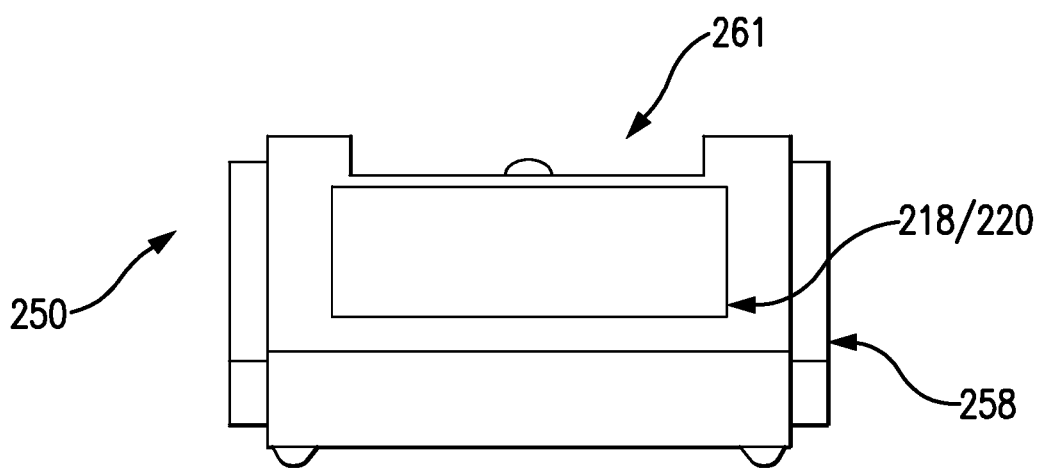
FIG. 17 is a front side view of the device of FIG. 14.
Figure 18:
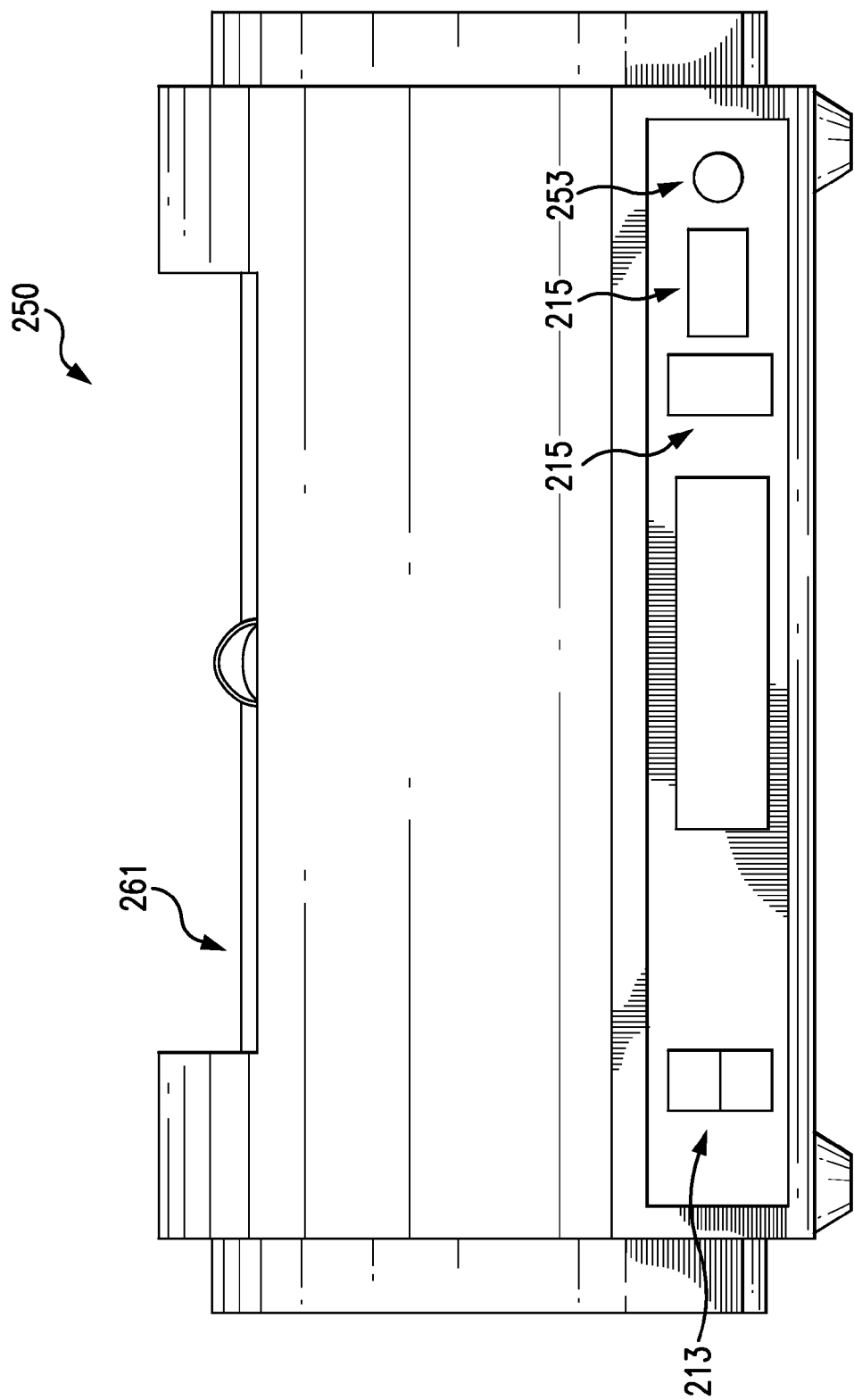
FIG. 18 is a rear side view of the device of FIG. 14.
Figure 19:
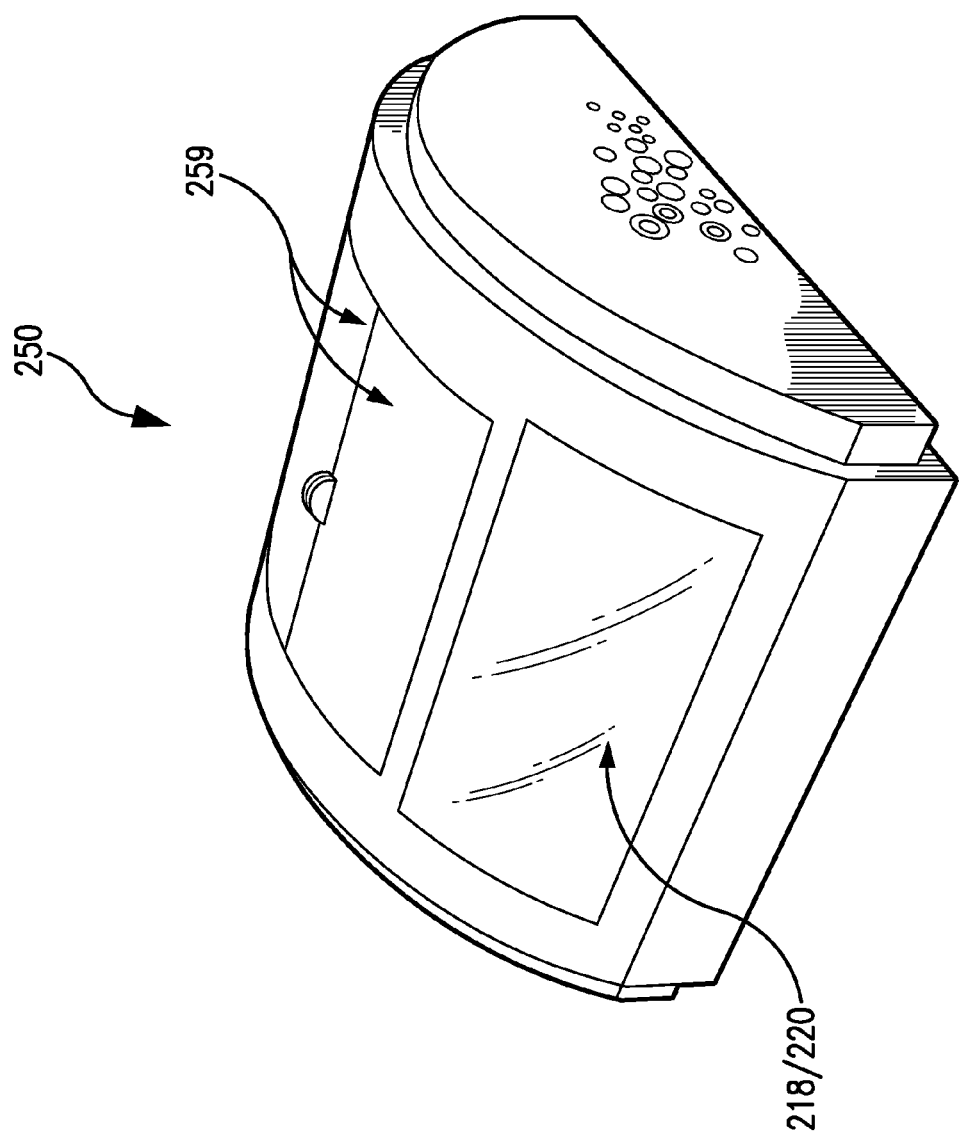
FIG. 19 shows the device of FIG. 14 with the access panels in a closed position.
Figure 20:
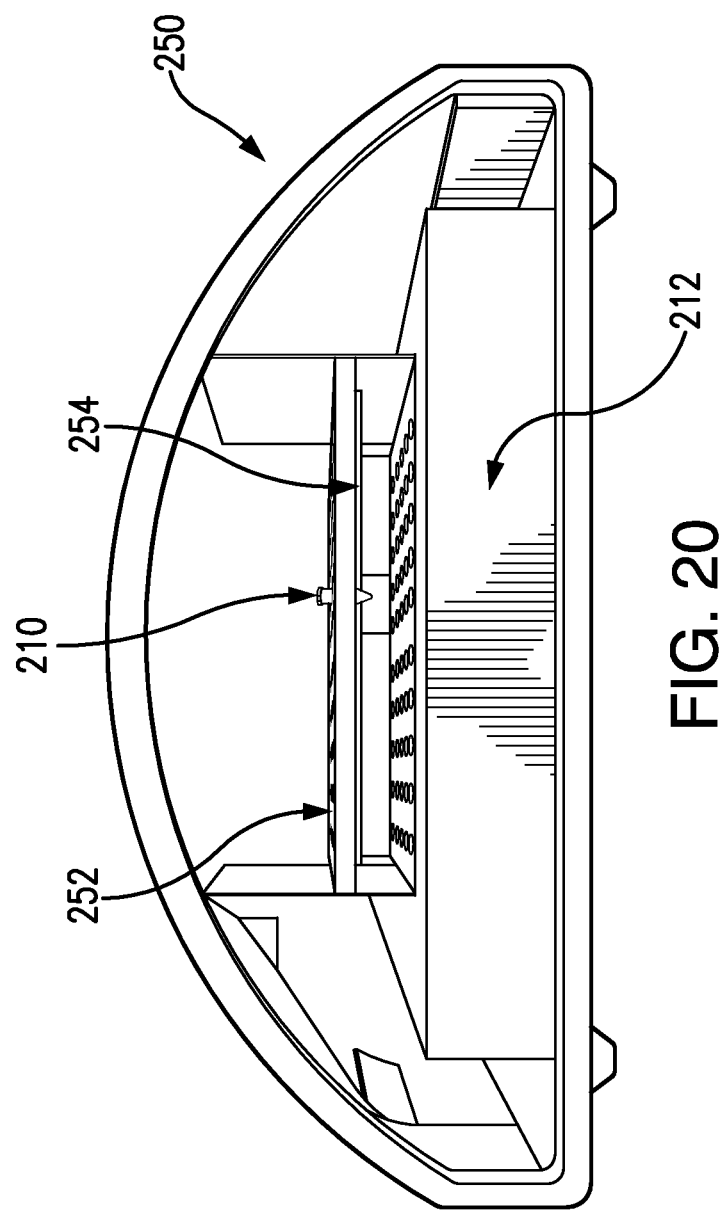
FIG. 20 shows the device of FIG. 15 with a portion of the housing removed to reveal the device's inner components.
Figure 21:
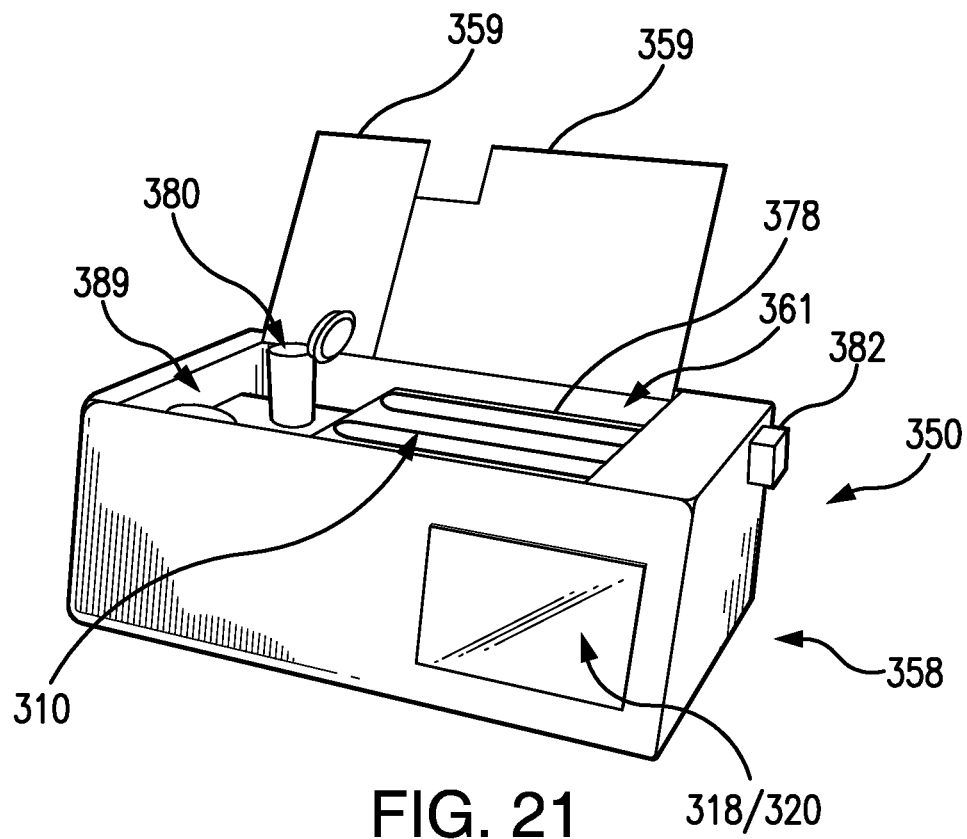
FIG. 21 is a perspective view of a device for amplifying nucleic acid according to a fourth example embodiment of the present invention, showing the access panels in an open position.
Figure 22:
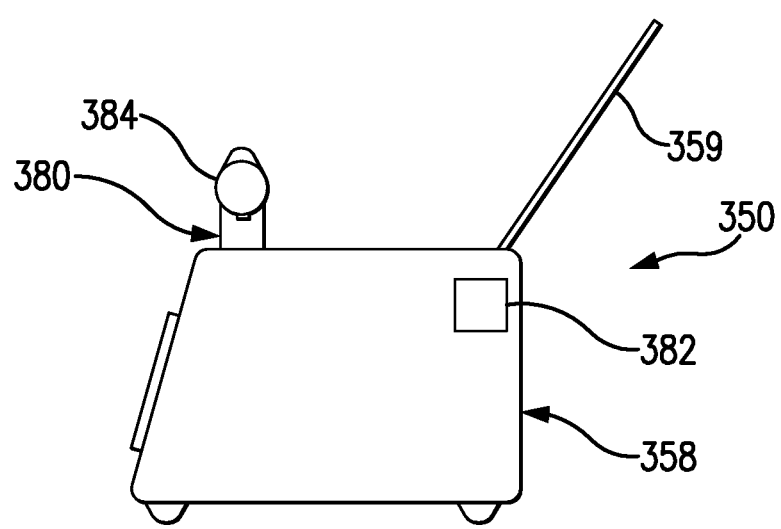
FIG. 22 is a right side view of the device of FIG. 21.
Figure 23:
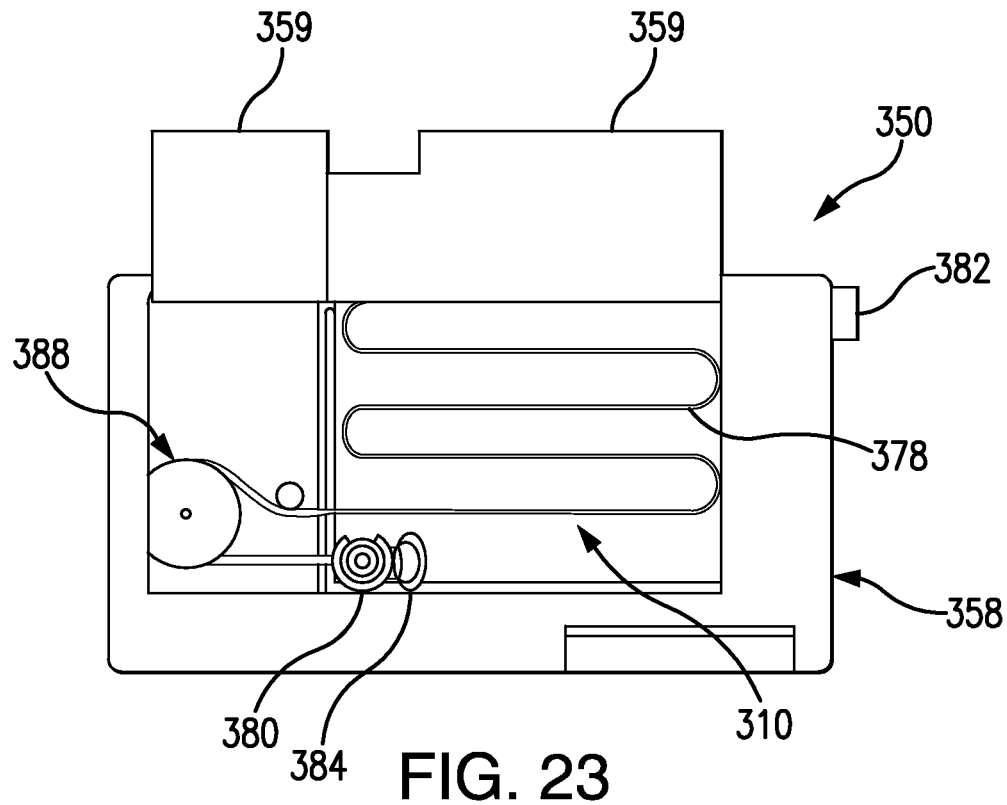
FIG. 23 is a top view of the device of FIG. 21.
Figure 24:
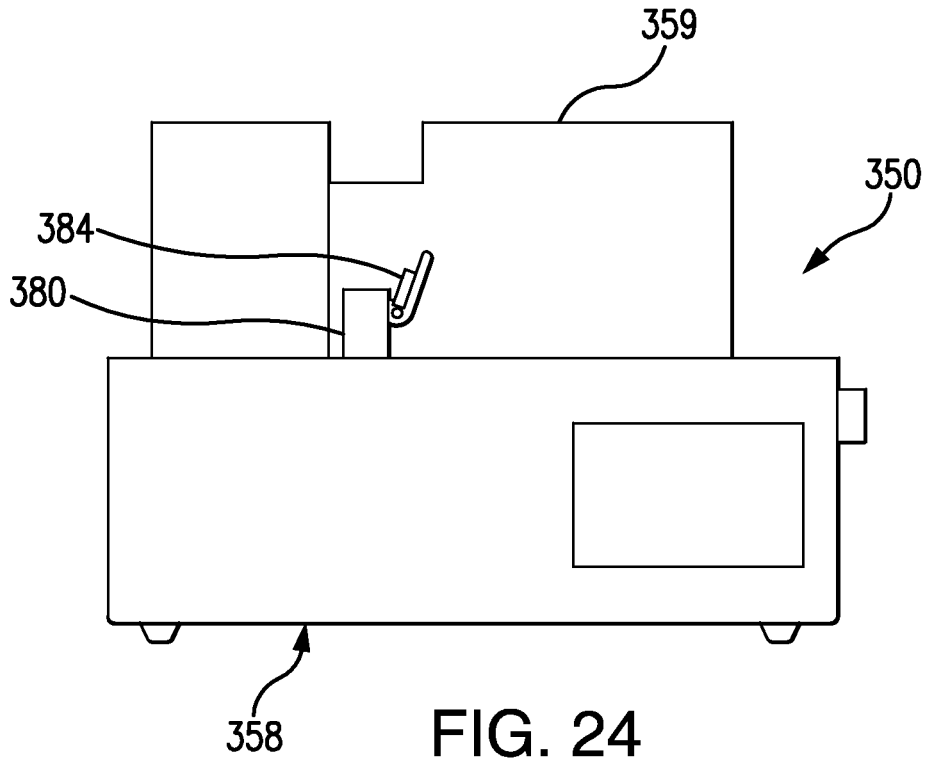
FIG. 24 is a front side view of the device of FIG. 21.
Figure 25:
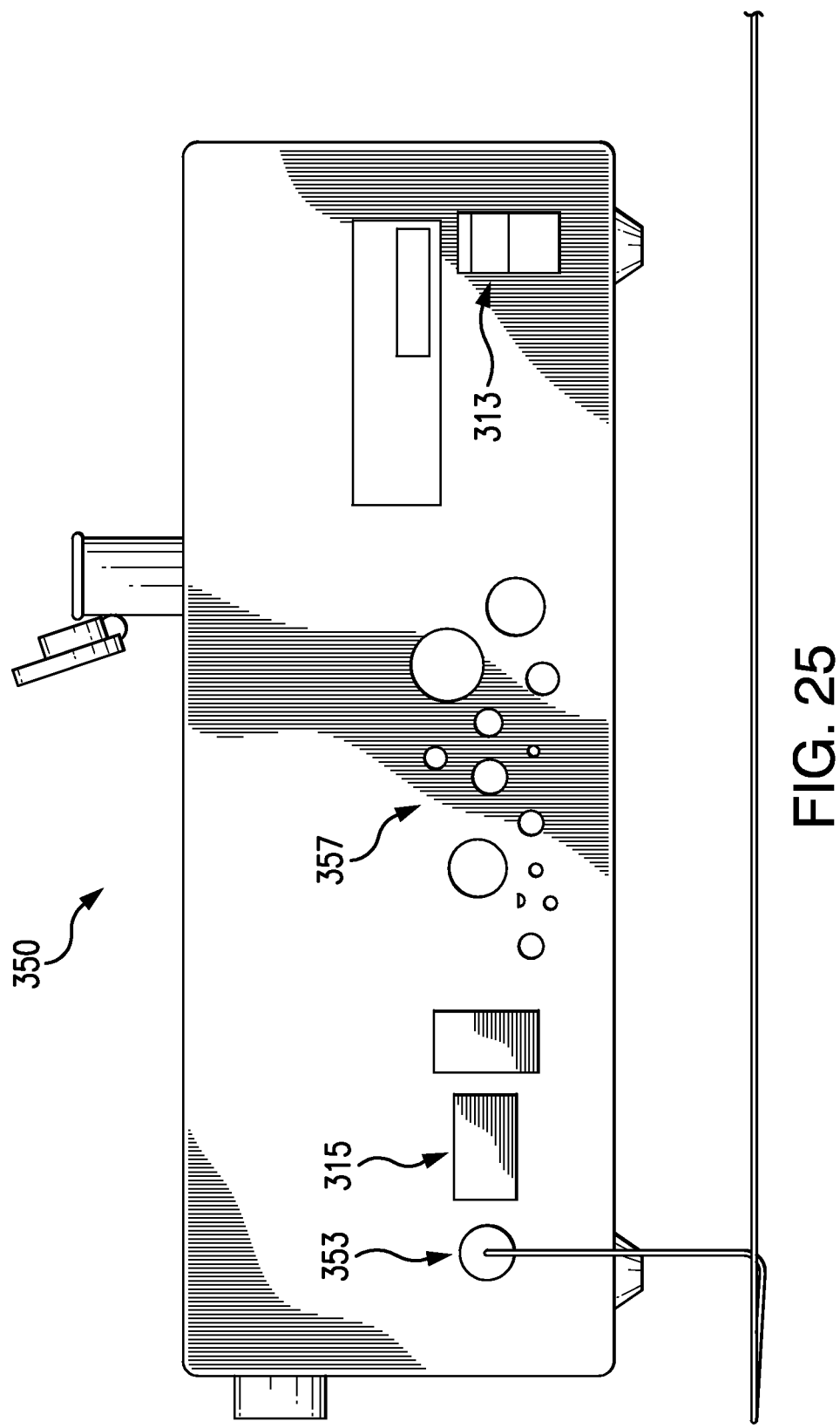
FIG. 25 is a rear side view of the device of FIG. 21.
Figure 26:
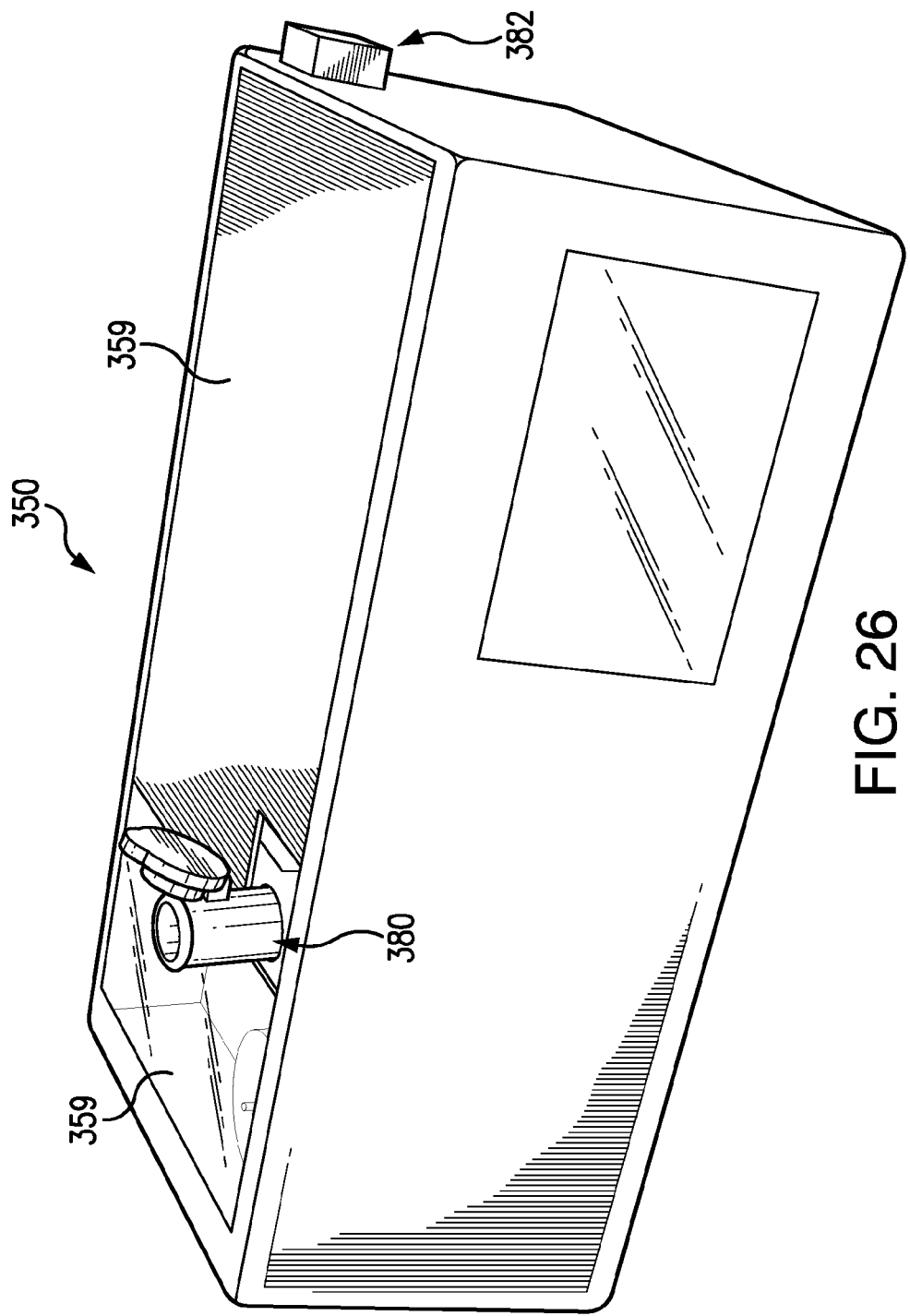
FIG. 26 shows the device of FIG. 21 with the access panels in a closed position.
Figure 27:
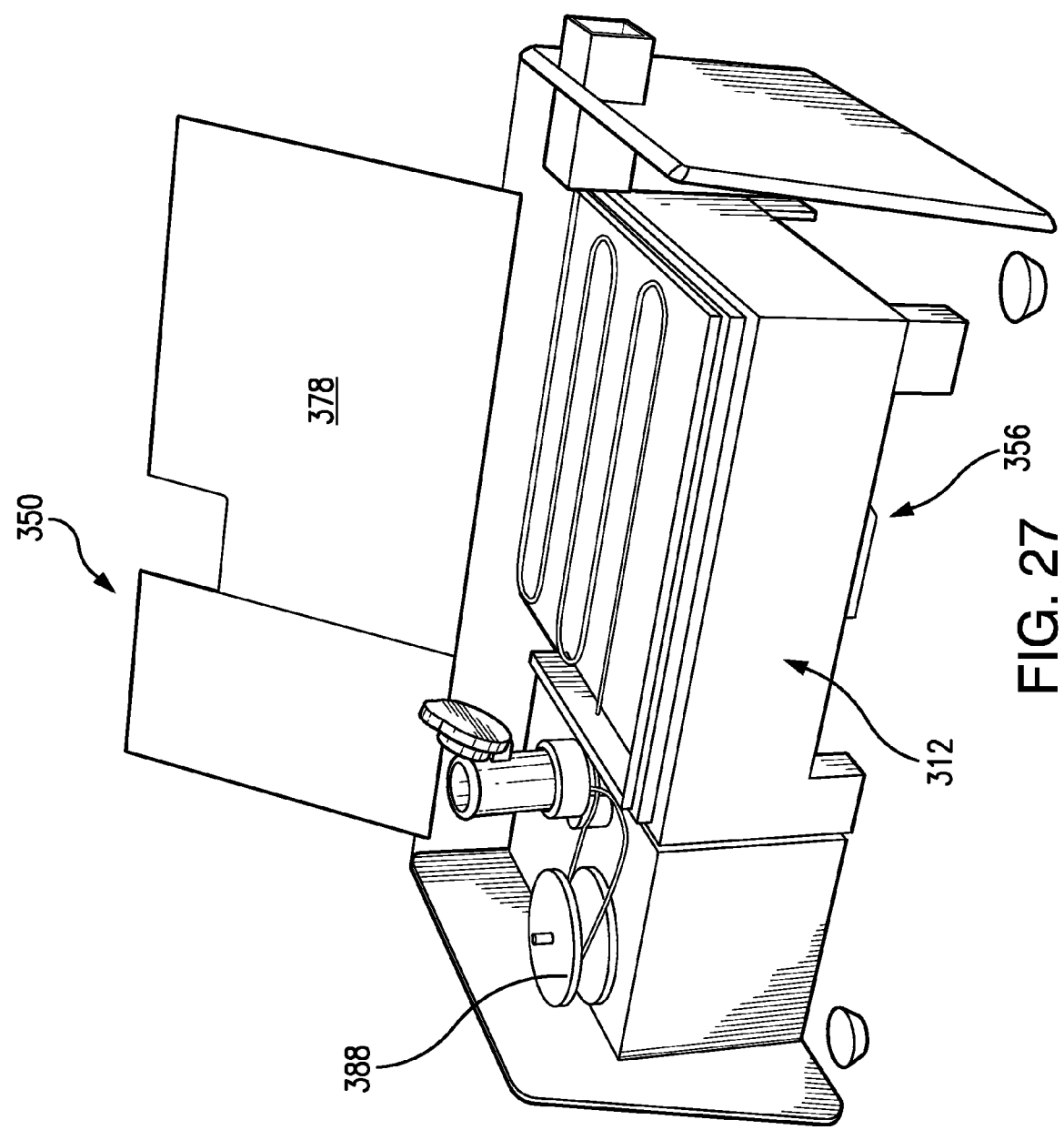
FIG. 27 shows the device of FIG. 2 with a portion of the housing removed to reveal the device's inner components.
Figure 28:
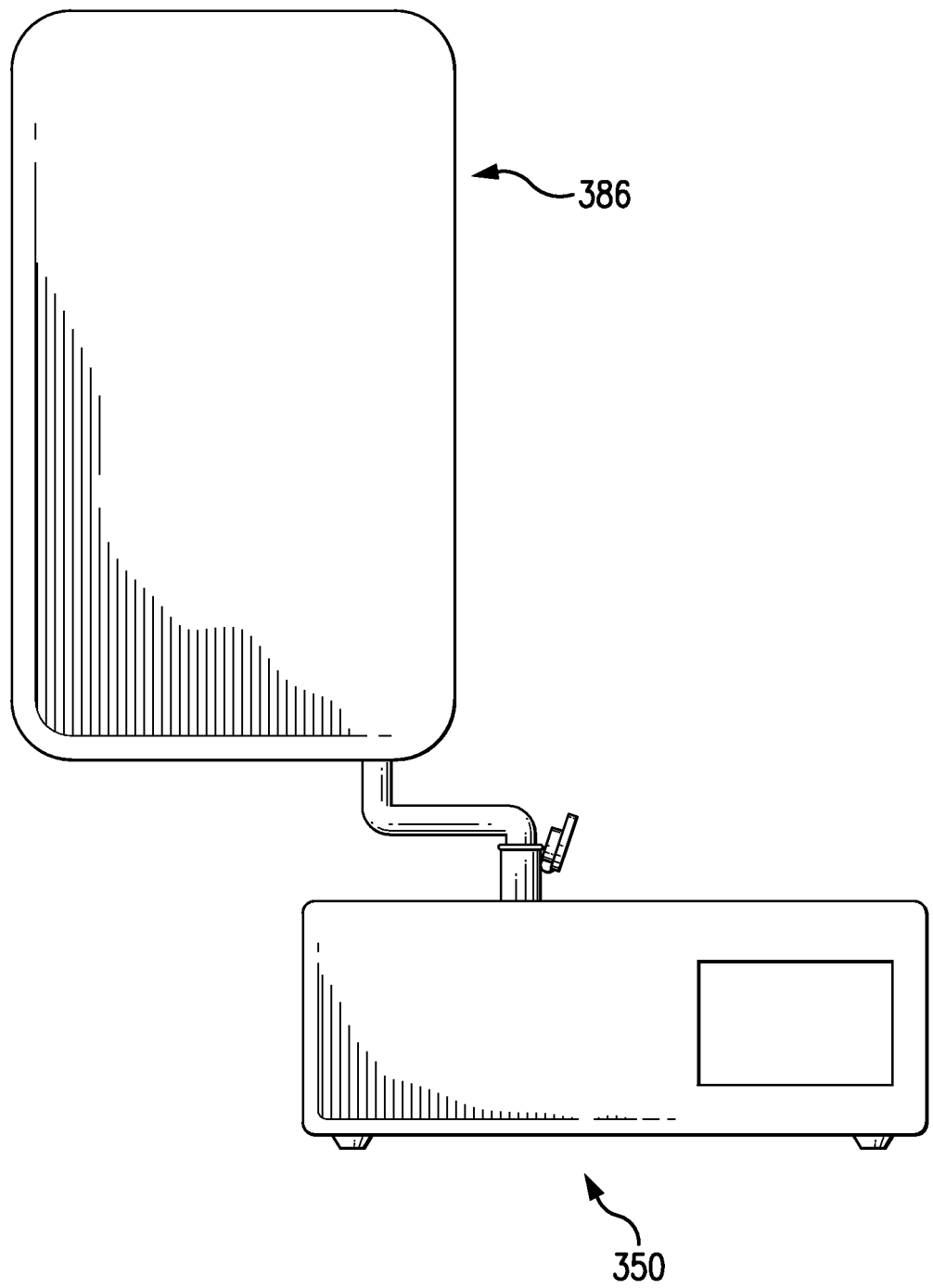
FIG. 28 is a front view of the device of FIG. 26 showing a sample tank continuously feeding the nucleic acid into the device.

FIG. 13 shows a device 150 for amplifying nucleic acid according to a second example embodiment of the present invention. The amplification device is substantially similar to that of the first embodiment. Thus, the amplification device 150 includes a circuit (not shown) that induces an electromagnetic field, a vial support 152 that supports vials 110 holding the nucleic acid samples, a control unit 112 for operating the circuit, and a housing 158 for all of these components. In addition, the amplification device 150 can, but does not necessarily have to, include a cooling system (not shown). In this embodiment, however, the control unit 112 is provided as an integral component of the amplification device 150 and is incorporated into the device housing 158.

The control unit 112 in this embodiment includes a power supply (not shown), control circuitry and/or programmed processor (not shown), one or more control inputs 118 such as the depicted keypad, and one or more control inputs 120 such as the display screen. These control unit 112 components are operable to control the voltage, current, time, and/or other operating parameters of the amplification device 150. Typically, these control unit 112 components, as well as the magnetic-field inducing circuit, the vial support 152, and the vials 110 held by the vial support, are all substantially similar to those of the above-described embodiment.

In this embodiment, the housing 158 additionally houses the control unit 112, so the housing is sized larger relative to that of the above-described embodiment. In addition, the housing 158 of this embodiment typically includes at least one access panel 159 that covers and partially defines a processing compartment in the housing 158 in which the vials 110 are held during operation of the amplification device 150. The access panel 159 can be in the form of a hinged lid, as depicted, that moves between a closed position (covering the processing compartment during operation of the amplification device 150) and an open position (for inserting and removing the vials 110).

FIGS. 14-20 show a device 250 for amplifying nucleic acid according to a third example embodiment of the present invention. The amplification device 250 is substantially similar to that of the second embodiment, in that the control unit 212 is provided as an integral component of the device and is incorporated into the device housing 258. Thus, the amplification device 250 includes a circuit 254 that induces an electromagnetic field, a vial support 252 that supports vials 210 holding the nucleic acid samples, the control unit 212 for operating the circuit, and the housing 258 for all of these components. Typically, these components are all substantially similar to those of the above-described second embodiment.

In this embodiment, however, the control unit 212 includes a combined input-output device 218/220 such as the depicted touch screen. Typically, the control unit 212 includes the power input connector 253, fuses for over-current protection 215, and an on-off switch 213. The components of the control unit 212 in typical commercial embodiments are selected for input voltages to the power supply of about 90 to 240 VAC, working voltages of about 12 VDC, and working power of about 30 W. In such embodiments, and with the vial support 252 configured for holding 100 vials 210, the amplification device 250 can typically be operated at a temperature of about 25 C to process the samples in the vials in a working time of between about 2 mins. and about 30 mins.

In addition, the housing 258 of this embodiment has a generally barrel-vault shape with two sliding access panels 259 that slide between the open and closed positions to cover and partially define the processing compartment 261 in the housing 258 in which the vials 210 are held during operation of the amplification device 250. Further, the housing 258 can include an array of ventilation openings 257 that form a part of a cooling system, which can additionally include at least one fan and controls for the fan. It should be noted that the dimensional and operating information in these drawings is representative of a typical commercial embodiment and is thus included for illustration purposes only and is not limiting of the invention.

FIGS. 21-32 show a device 350 for amplifying nucleic acid according to a fourth example embodiment of the present invention. The amplification device 350 is similar to those of the previously described embodiments in that it includes a circuit 354 that induces an electromagnetic field and a control unit 312 for operating the circuit, and typically includes a cooling system 356 as well as a housing 358 for all of these components. Typically, these components are all substantially similar to those of the above-described embodiments.

In this embodiment, however, the device 350 is designed for continuous processing of the nucleic acid, instead of the batch-processing designs of the above-described embodiments. Thus, instead of a vial support for holding an array of individual vials containing respective discrete nucleic acid samples to be processed in batches, the device 350 includes at least one tube 310 that carries the nucleic acid. The tube 310 includes a working portion 378 of the tube in the processing compartment 361 of the housing 358, an inlet portion 380, and an outlet portion 382. The inlet 380 typically includes a closure 384, for example a friction-fit lid (as depicted) or a screw-on lid, that can be removed to connect to a tank 386 holding the nucleic acid sample. In addition, the inlet 380 can include interchangeable end fittings for adapting to different sizes of discharge hoses of sample tanks 386. And the outlet 382 typically includes a closure, for example a friction-fit lid or a screw-on lid, that can be removed to connect to a spectrophotometer for analysis of the nucleic acid sample, a storage tank, or another post-amplification device. The inlet 380 and the outlet 382 are typically closed when the device 350 is not in use to avoid contamination of the inside of the tube 376. The working portion 378, inlet portion 380, and outlet portion 382 of the tube 310 can be provided by conventional tubing or hosing that is well known in the art. In typical commercial embodiments, for example, the tube 310 is made of silicon or TEFLON material.

When using this continuous-processing amplification device 350, a supply tank 386 holding the nucleic acid to be amplified is connected to the inlet 380 and the nucleic acid is flowed through the tube working portion 378 to provide the desired residence time for the exposure of the nucleic acid to the magnetic field in the PCR process. The tube working portion 378 has a diameter and length selected, in conjunction with the flow rate of the nucleic acid, to provide the desired residence time of the nucleic acid sample for exposure to the magnetic field. In the depicted embodiment, for example, the tube working portion 378 has a diameter of 1 mm and a length of 75 cm. For this embodiment, the residence time is typically about 2 mins. to about 30 mins. when the amplification device 350 is operated at a temperature of about 25 C. To accomplish this, the flow rate of the nucleic acid sample through the tube working portion 378 is typically about 37.5 µl/min. to about 1.25 µl/min, respectively. In other embodiments, the tube working portion 378 has a diameter and length that are larger or small, the operating temperature is higher or lower, and/or the flow rate of the nucleic acid sample through the tube working portion is increased or decreased, to provide the desired residence time. In typical embodiments such as that depicted, one tube working portion 378 is arranged in a serpentine or sinusoidal configuration to provide the desired length in a compact manner. In other embodiments, the tube working portion is arranged in a helical, spiral, or other configuration, and/or multiple tube working portions are included. The amplification device 350 includes a pump 388 to cause the nucleic acid to flow through the tube 311. The pump 388 can be of a convention type such as a peristaltic pump for providing the flow rates disclosed above. In typical embodiments such as that depicted, the pump 388 is operably connected to the tube 311 between its inlet 380 and its working portion 378. The pump 388 can be operated continuously so that the nucleic acid is constantly flowed through the tube working portion 378, or it can be operated intermittently to increase the residence time of the nucleic acid's exposure to the magnetic field. In other embodiments, the amplification device is provided without a pump and the inlet and outlet are positioned for gravity flow of the nucleic acid through the tube working portion.

The electromagnetic field-inducing circuit 354 includes the conductor 368 and typically also includes resistors as noted above. In typical embodiments, the amplification device includes a tube support 352 to which the conductor 368 and the tube working portion 378 are mounted at a fixed separation distance. For example, the tube support 352 can be provided by a plate with the conductor 368 mounted on its bottom side and with the tube working portion 378 mounted on its top side at a separation of about 7 mm, as depicted. The tube-support plate 352 can be made of a material such as polystyrene or BAKELITE material. The tube-support plate 352 can include channels 390 that receive the conductor 368 and the tube working portion 378 in their fixed positions and hold them in place. The conductor 368 and the tube working portion 378 are positioned equidistantly along their entire lengths, for example vertically aligned in conforming arrangements, to provide a uniform exposure of the nucleic acid to the magnetic field. For example, when the tube working portion 378 is arranged in serpentine configuration, the conductor 368 can be arranged in a conforming serpentine configuration so that the two are aligned and equidistantly separated along their entire lengths, as depicted. In other embodiments, the conductor is coiled around the tube working portion and/or multiple conductors are provided for each tube.

In addition, in this embodiment the control unit 312 includes a combined input-output device 318/320 such as the depicted touch screen. Typically, the control unit 312 includes the power input connector 353, fuses for over-current protection 315, and an on-off switch 313. The components of the control unit 312 in typical commercial embodiments are selected for input voltages to the power supply of about 90 to 240 VAC, working voltages of about 12 VAC, and working power of about 30 W. In such embodiments, examples of the approximate mini-current I and the magnetic field B are the same as those listed above in Tables 1 and 2 for the first embodiment, and additionally can include those approximate values listed below in Tables 3-6. Each of the ranges between each of the listed approximate values (referring to Tables 3-6 collectively) is considered to represent a separate embodiment and mode of use. And as with Tables 1 and 2, the magnetic field B is the strength of the magnetic field at and applied to the samples in the tube 310, which is necessarily less than the core magnetic field immediately adjacent the conductor 368 inducing it due to the distance spacing "d" between the conductor and the tube axial centerline. Note that the distance d is the conductor-to-tube-centerline spacing, subject to the conditions described with respect to the first embodiment above.

In Table 3, the voltage and current I were varied to produce various magnetic fields B on the samples to assess the resulting amplification. And in Tables 4-6, the voltage and resistance were varied to produce the same current I and magnetic field B on the samples to assess different design and construction options. In all four Tables, the distance "d" is 7 mm.

TABLE 3

| Working Voltage (V) | Mini-Current I (Amps) | Magnetic Field B (Gauss) |
|---|---|---|
| 0.01 | 0.005 | 0.001 |
| 0.05 | 0.025 | 0.009 |
| 0.1 | 0.05 | 0.019 |
| 0.2 | 0.10 | 0.039 |
| 0.3 | 0.15 | 0.059 |
| 0.4 | 0.20 | 0.080 |
| 0.5 | 0.25 | 0.100 |
| 0.6 | 0.30 | 0.120 |
| 0.7 | 0.35 | 0.141 |
| 0.8 | 0.40 | 0.161 |
| 0.9 | 0.45 | 0.180 |
| 1.0 | 0.50 | 0.200 |
| 1.2 | 0.60 | 0.241 |
| 1.4 | 0.70 | 0.282 |
| 1.5 | 0.80 | 0.322 |
| 1.8 | 0.90 | 0.360 |
| 2.0 | 0.90 | 0.360 |
| 2.0 | 1.00 | 0.402 |
| 2.4 | 1.20 | 0.480 |
| 3.0 | 1.50 | 0.610 |

TABLE 4

| Working Voltage (VDC) | Mini-Current I (Amps) | Resistance (Ohms) | Magnetic Field B (Gauss) |
|---|---|---|---|
| 0.5 | 1.0 | 0.5 | 0.402 |
| 1.0 | 1.0 | 1.0 | 0.402 |
| 1.5 | 1.0 | 1.5 | 0.402 |
| 2.0 | 1.0 | 2.0 | 0.402 |
| 2.5 | 1.0 | 2.5 | 0.402 |
| 3.0 | 1.0 | 3.0 | 0.402 |
| 3.5 | 1.0 | 3.5 | 0.402 |
| 4.0 | 1.0 | 4.0 | 0.402 |
| 4.5 | 1.0 | 4.5 | 0.402 |
| 5.0 | 1.0 | 5.0 | 0.402 |
| 5.5 | 1.0 | 5.5 | 0.402 |
| 6.0 | 1.0 | 6.0 | 0.402 |
| 6.5 | 1.0 | 6.5 | 0.402 |
| 7.0 | 1.0 | 7.0 | 0.402 |
| 7.5 | 1.0 | 7.5 | 0.402 |
| 8.0 | 1.0 | 8.0 | 0.402 |
| 8.5 | 1.0 | 8.5 | 0.402 |
| 9.0 | 1.0 | 9.0 | 0.402 |
| 9.5 | 1.0 | 9.5 | 0.402 |
| 10.0 | 1.0 | 10.0 | 0.402 |
| 10.5 | 1.0 | 10.5 | 0.402 |
| 11.0 | 1.0 | 11.0 | 0.402 |
| 11.5 | 1.0 | 11.5 | 0.402 |
| 12.0 | 1.0 | 12.0 | 0.402 |

TABLE 5

| Working Voltage (VDC) | Mini-Current I (Amps) | Resistance (Ohms) | Magnetic Field B (Gauss) |
|---|---|---|---|
| 0.5 | 1.2 | 0.42 | 0.48 |
| 1.0 | 1.2 | 0.83 | 0.48 |
| 1.5 | 1.2 | 1.25 | 0.48 |
| 2.0 | 1.2 | 1.67 | 0.48 |
| 2.5 | 1.2 | 2.083 | 0.48 |
| 3.0 | 1.2 | 2.50 | 0.48 |
| 3.5 | 1.2 | 2.92 | 0.48 |
| 4.0 | 1.2 | 3.33 | 0.48 |
| 4.5 | 1.2 | 3.75 | 0.48 |
| 5.0 | 1.2 | 4.17 | 0.48 |
| 5.5 | 1.2 | 4.58 | 0.48 |
| 6.0 | 1.2 | 5.00 | 0.48 |
| 6.5 | 1.2 | 5.42 | 0.48 |
| 7.0 | 1.2 | 5.83 | 0.48 |
| 7.5 | 1.2 | 6.25 | 0.48 |
| 8.0 | 1.2 | 6.67 | 0.48 |
| 8.5 | 1.2 | 7.08 | 0.48 |
| 9.0 | 1.2 | 7.50 | 0.48 |
| 9.5 | 1.2 | 7.92 | 0.48 |
| 10.0 | 1.2 | 8.33 | 0.48 |
| 10.5 | 1.2 | 8.75 | 0.48 |
| 11.0 | 1.2 | 9.17 | 0.48 |
| 11.5 | 1.2 | 9.58 | 0.48 |
| 12.0 | 1.2 | 10.0 | 0.48 |

TABLE 6

| Working Voltage (VDC) | Mini-Current I (Amps) | Resistance (Ohms) | Magnetic Field B (Gauss) |
|---|---|---|---|
| 0.5 | 1.5 | 0.33 | 0.61 |
| 1.0 | 1.5 | 0.67 | 0.61 |
| 1.5 | 1.5 | 1.00 | 0.61 |
| 2.0 | 1.5 | 1.33 | 0.61 |
| 2.5 | 1.5 | 1.67 | 0.61 |
| 3.0 | 1.5 | 2.00 | 0.61 |
| 3.5 | 1.5 | 2.33 | 0.61 |
| 4.0 | 1.5 | 2.67 | 0.61 |
| 4.5 | 1.5 | 3.00 | 0.61 |
| 5.0 | 1.5 | 3.33 | 0.61 |
| 5.5 | 1.5 | 3.67 | 0.61 |
| 6.0 | 1.5 | 4.00 | 0.61 |
| 6.5 | 1.5 | 4.33 | 0.61 |
| 7.0 | 1.5 | 4.67 | 0.61 |
| 7.5 | 1.5 | 5.00 | 0.61 |
| 8.0 | 1.5 | 5.33 | 0.61 |
| 8.5 | 1.5 | 5.67 | 0.61 |
| 9.0 | 1.5 | 6.00 | 0.61 |
| 9.5 | 1.5 | 6.33 | 0.61 |
| 10.0 | 1.5 | 6.67 | 0.61 |
| 10.5 | 1.5 | 7.00 | 0.61 |
| 11.0 | 1.5 | 7.33 | 0.61 |
| 11.5 | 1.5 | 7.67 | 0.61 |
| 12.0 | 1.5 | 8.00 | 0.61 |

In a preferred embodiment, the PCR device 350 is operated with good results with a mini-current I of about 900 mA to induce a magnetic field B of about 0.35 to about 0.36 Gauss on the nucleic acid sample in the tubes 310 carrying it when the tube and the magnetic-field-inducing conductor 368 are uniformly positioned relative to each other and uniformly spaced apart by a distance d of, for example, about 7.0 mm. In other preferred embodiments, the PCR device 350 is operated with a mini-current I of about 0.8 A to induce a magnetic field B of about 0.322 Gauss on the sample, with a mini-current I of about 1.0 A to induce a magnetic field B of about 0.402 Gauss on the sample, or with a mini-current I and a magnetic field B within the ranges defined by those approximate values. In still other preferred embodiments, the PCR device 350 is operated with a mini-current I of about 1.2 A to induce a magnetic field B of about 0.48 Gauss on the sample or with a mini-current I of about 1.5 A to induce a magnetic field B of about 0.61 Gauss on the sample. And in still other preferred embodiments, the PCR device 350 is operated with a mini-current I within the range of about 1.0 A to about 1.2 A, about 1.2 A to about 1.5 A, or about 1.0 A to about 1.5 A, to induce a magnetic field B on the sample within the range of about 0.402 Gauss to about 0.48 Gauss, about 0.48 Gauss to about 0.61 Gauss, or about 0.402 Gauss to about 0.61 Gauss, respectively.

It will be understood that the PCR device 350 can be operated to induce a magnetic field B on the sample of higher or lower strengths to produce the intended results as described herein. In some embodiments, for example, the magnetic-field-inducing conductor 368 is spaced a different distance d (than the 7.0 mm spacing of the depicted embodiment) from the centerline of the tube 310 carrying the sample, and/or a current I of a different strength is passed through the conductor 368 (by using a different voltage and/or resistance), so that a magnetic field B of different strength is induced by the conductor and applied to the sample. Typically, for a decreased conductor-to-sample distance d and/or a stronger current I, a stronger magnetic field B is induced, and for an increased conductor-to-sample spacing and/or a weaker current, a weaker magnetic field is induced, to produce the desired amplification.

In other embodiments, a core magnetic field of a different strength is induced to apply the same-effect magnetic field B to the samples. For example, in some embodiments the magnetic-field-inducing conductor 368 is spaced a different distance d (than the 7.0 mm spacing of the depicted embodiment) from the tube 310 holding the samples, so a current I of a different strength is passed through the conductor 368 (by using a different voltage and/or resistance) in order to induce a core magnetic field of a different strength such that, given the different conductor-to-sample spacing, the magnetic field B at and applied to the sample is still in the same range of about 0.322 Gauss to about 0.402 Gauss. And in other embodiments, a current I of a different strength is passed through the conductor 68, so a core magnetic field of a different strength is induced, and in order for the magnetic field B at and applied to the samples to be still in the same preferred range of about 0.322 Gauss to about 0.402 Gauss, a different conductor-to-sample distance spacing d is used.

In order to determine the conductor-to-sample distance spacing d and the current I to provide a magnetic field B at and applied to the samples in for example the preferred range of about 0.322 Gauss to about 0.402 Gauss, the same Biot and Savat equation (described above with respect to Tables 1 and 2) is used in the same fashion.

Furthermore, the housing 358 of this embodiment can include an array of ventilation openings 357 that form a part of a cooling system 356, which can additionally include at least one fan and controls for the fan. Also, the housing 358 can include two separately movable access panels 359 that cover and partially define the processing compartment 361 and a pump compartment 389. The access panels 359 can be in the form of hinged lids, as depicted, that move between a closed position (covering the processing and pump compartments during operation of the amplification device 350) and an open position (for accessing the tube working portion 378 and the pump 388). It should be noted that the dimensional and operating information in these drawings is representative of a typical commercial embodiment and is thus included for illustration purposes only and is not limiting of the invention.

In another embodiment, the PCR device includes at least one magnetic-field-inducing circuit and at least one heating element in a combination design, with the heating elements being of a conventional type known in the art. In yet another embodiment, the PCR device includes a magnetic-field-inducing circuit (with or without any heating elements) and is operated at higher currents (higher than the mini-current described above) to generate sufficient heat sufficiently close to the sample to materially impact the PCR process. In these embodiments, the PCR device amplifies the nucleic acid by the application of the magnetic field and heat in a combination of a magnetic-field process and a thermal process. As such, these combination devices are not operable to produce a thermal-free PCR process. For example, testing was done by placing one of the PCR electromagnetic devices inside a closed chamber that is able to maintain a constant temperature, then setting the chamber temperature above and below ambient temperature (25° C.), such as at 10° C., 15° C., 20° C., 30° C., 35° C., 40° C., 45° C., 50° C., and 55° C. This testing showed that the PCR device can work with generally good results when small amounts of heat (relative to conventional PCR systems) are applied to the sample being amplified. So designs combining both heat and an electromagnetic field are contemplated by and included within the present invention.

II. Methods for Amplifying Nucleic Acids

Described herein are methods for amplifying nucleic acids. The methods generally involve exposing the nucleic acid to an electromagnetic field, for example a mini-current magnetic field, while performing the steps of PCR. In one aspect, the method involves exposing the nucleic acid to a mini-current magnetic field for a sufficient time and amount to amplify the nucleic acid. In certain aspects, a primer, a polymerase, or a combination thereof can be used during the method; however, these components are optional.

The process is carried out using a PCR amplification device that uses an electromagnetic field to carry out the PCR process. For example, the PCR amplification devices described herein can be used to carry out the PCR process. When using a batch-processing device, the nucleic acid to be amplified is placed in one or more vials. The vials can be of the type described above. Thus, the volume of the sample tubes can be 0.2 mL, 0.6 mL, 1.0 mL, 1.5 mL, or 2.0 mL. The thickness of the tube wall can be 0.5 mm to 1.5 mm, preferably 1.15 mm to 1.20 mm, or more preferably 1.17 mm. The wall thickness of the sample tube can be varied in order to maximize magnetic field distribution. When using a continuous-processing device, a tank of the nucleic acid to be amplified is connected to the device and the nucleic acid is flowed through the tubing in the device. The nucleic acid can be any molecule where it is possible and desirable to amplify (i.e., generating multiple copies of a specific nucleic acid sequence). In one aspect, the nucleic acid can be an oligonucleotide, deoxyribonucleic acid (DNA), ribonucleic acid (RNA), or peptide nucleic acid (PNA). The nucleic acid of interest introduced by the present method can be a nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature. In one aspect, the DNA can be genomic DNA. In other aspects, the DNA can be double-stranded DNA including, but not limited to, a plasmid (linear or coiled, etc.), cosmid, phage, viral, YACS, BACS, other artificial chromosomes, and the like). Alternatively, the DNA can be single stranded.

In one aspect, the nucleic acid can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, sRNA, miRNA, shRNA and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acids can be a small gene fragment that encodes dominant-acting synthetic genetic elements (SGEs), e.g., molecules that interfere with the function of genes from which they are derived (antagonists) or that are dominant constitutively active fragments (agonists) of such genes. SGEs can include, but are not limited to, polypeptides, inhibitory antisense RNA molecules, ribozymes, nucleic acid decoys, and small peptides. The small gene fragments and SGE libraries disclosed in U.S. Patent Publication No. 2003/0228601, which is incorporated by reference, can be used herein.

In general, the methods described herein involve the application of an electromagnetic field to a sample containing the nucleic acid and, optionally, a primer and/or polymerase in the absence of applied heat in order to amplify a nucleic acid sequence of interest. Typically, the methods typically involve the application of a mini-current magnetic field to the sample in the absence of applied heat. Thus, the reaction is typically performed at a constant temperature of less than or equal to about 30° C., preferably less than or equal to about 25° C. The magnitude and duration of the magnetic field applied to the nucleic acid can vary. For example, the magnitude of the magnetic field applied in steps (a) and (b) above can be the same or different. Similarly, the duration of exposure to the magnetic field can be the same or different in steps (a) and (b). Different voltages can be used including different mini-currents to induce the magnetic field B by the magnetic-field inducing circuit. In one aspect, the voltage/mini-current is 50 mV/25 mA, 100 mV/50 mA, 150 mV/80 mA, 200 mV/100 mA, 250 mV/100 mA, 300 mV/150 mA, 500 mV/250 mA, 800 mV/400 mA, 1000 mV/500 mA, 1500 mV/800 mA, or 2000 mV/1000 mA. In another aspect, the voltage and mini-current in steps (a) and (b) are from 50 mV to 2,000 mV and from 25 mA to 1,000 mA. In another aspect, the voltage and mini-current in steps (a) and (b) are from 800 mV to 1,000 mV and from 400 mA to 500 mA. In a further aspect, the duration of exposure of the nucleic acid to the magnetic field B in steps (a) and (b) can range from 5 minutes to 60 minutes, from 5 minutes to 50 minutes, from 5 minutes to 40 minutes, from 5 minutes to 30 minutes, or from 5 minutes to 20 minutes. When using a batch-processing device, the vials containing the nucleic acid are held in place on the vial support for the duration of exposure of the nucleic acid to the magnetic field B in steps (a) and (b). When using a continuous-processing device, the nucleic acid is flowed through the tubing in the device at a rate selected to achieve a residence time for the duration of exposure of the nucleic acid to the magnetic field B in steps (a) and (b). In addition, the proportions of the reagents used in the reaction are the same whether using the batch-processing device or the continuous-processing device, however, the volumes of the final reaction mix typically can be in the range of about 10 µl to about 1000 liters when using the continuous-processing device. In yet another aspect, the magnetic field B induced by the mini-current is about 0.35 or about 0.36 Gauss. In a typical use of the method, the voltage is about 12V and the mini-current is about 900 mA, and the induced magnetic field B is about 0.35 Gauss. Devices for generating the mini-current magnetic field and exposing the sample of nucleic acid to the magnetic field are described in detail above.

The sample of nucleic acid can be prepared using techniques known in the art for preparing samples used in conventional PCR techniques. For example, the nucleic acid can be dissolved in water and buffer, where the buffered solution contains a divalent cation such as $Ca^{+2}$ or $Mg^{+2}$. One significant difference regarding sample preparation is that in the methods described herein, when a primer and/or polymerase are used, they can be added directly to the sample containing the nucleic acid. This is not the case with conventional PCR. For example, if the nucleic acid is double-stranded DNA, the first step in conventional PCR involves the denaturing of the DNA by heat in the absence of the primer. It is only after the DNA is denatured that the primer is added to the sample followed by a second heating cycle. Thus, the methods described herein are more efficient compared to conventional PCR, where an additional step is required prior to annealing the primer to the DNA.

The primers useful herein can be an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced. The primer is preferably single stranded for maximum efficiency in amplification, but may alternatively be double stranded. If double stranded, the primer is first treated to separate its strands before being used to prepare extension products. The primer should be sufficiently long to prime the synthesis of extension products in the presence of the polymerase. For example, depending on the complexity of the target sequence, the oligonucleotide primer typically contains 15-25 or more nucleotides, although it may contain more or fewer nucleotides.

The primers herein are selected to be "substantially" complementary to the different strands of each specific sequence to be amplified. This means that the primers should be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to be amplified to hybridize therewith and thereby form a template for synthesis of the extension product of the other primer. However, for detection purposes, particularly using labeled sequence-specific probes, the primers typically have exact complementarity to obtain the best results.

If a primer is used in the methods described herein and has annealed to the nucleic acid of interest, a polymerase can be added to the sample containing the annealed nucleic acid, and the sample is exposed to the mini-current magnetic field for a sufficient time and duration in order to extend or elongate the sequence of interest. Polymerases are enzymes that assist in the polymerization of new DNA or RNA against an existing DNA or RNA template in the PCR process. When the nucleic acid is DNA, a DNA polymerase of the types I-V can be used herein. Alternatively, when RNA is the nucleic acid, RNA polymerases such as type I-III and T7 RNA polymerase can be used. Another advantage of the methods described herein is that lower amounts of polymerase are required compared to conventional PCR techniques. For example, the methods described can use 0.3 □L or 0.5 □L of polymerase. Thus, in one aspect, the amount of polymerase used herein is up to 50% or 70% less than the amount needed in conventional PCR techniques.

The methods described herein can be used in any application where conventional PCR is used. For example, the methods described herein permit the isolation of DNA fragments from genomic DNA by selective amplification of a specific region of DNA. Thus, hybridization probes for Southern or northern hybridization and DNA cloning, which require larger amounts of DNA, can be produced by the methods described herein.

The methods described herein can be used to analyze extremely small amounts of sample. This is often critical for forensic analysis, when only a trace amount of DNA is available as evidence. Any type of organism can be identified by examination of DNA sequences unique to that species. Applications of the methods described herein with respect to forensics include, but are not limited to, identifying potential suspects whose DNA may match evidence left at crime scenes, exonerating persons wrongly accused of crimes, identifying crime and catastrophe victims, establish paternity and other family relationships, identifying endangered and protected species as an aid to wildlife officials (could be used for prosecuting poachers), detecting bacteria and other organisms that may pollute air, water, soil, and food, match organ donors with recipients in transplant programs, determine pedigree for seed or livestock breeds, authenticate consumables such as caviar and wine, and analyze ancient DNA that is tens of thousands of years old.

PCR permits early diagnosis of malignant diseases such as leukemia and lymphomas, which is currently the highest-developed in cancer research and is already being used routinely. PCR assays can be performed directly on genomic DNA samples to detect translocation-specific malignant cells at a very high sensitivity.

The methods described herein are useful in the discovery and design of new pharmaceuticals. The fact that the methods can amplify higher amounts of nucleic acid compared to conventional PCR techniques, it is possible to produce greater amounts of potential pharmaceuticals that can be evaluated as potential drug candidates. Additionally, the fact that the methods require no heating step and can be performed in much shorter times compared to conventional PCR, it is possible to generate more potential drug candidates in a cost-effective manner. Moreover, the methods described herein can be used as an analytical tool to evaluate the content and purity of nucleic acids when deigning and synthesizing new drugs. In summary, the methods described herein can substitute conventional PCR in any application related to drug design and analytical evaluation thereof.

In certain aspects, the methods described herein can be used to amplify and simultaneously quantify a target nucleic acid in real time (i.e., quantitative real time polymerase chain reaction or qPCR). The detection of target DNA can be performed by the use of (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

In one aspect, the optical device useful for qPCR and RealTime analysis includes a light source of emission, a specific filter within 450 and 520 nm of wave length, and a detection system designed to couple to the system to read fluorescence produced by probes such as, for example, SYBRgreen or taqman probes present in the sample vials prior to exposing the sample to the magnetic field. The system can be adapted to read each sample independently during the during amplification process over time. The bottom of the cell can be configured with dark walls in order to avoid interference of media light and from side samples. Measurements can be taken during the amplification process, and the detector transducer can change the signal into a fluorescence value that is correlated with a standard curve to determine number of copies produced during the amplification process.

The methods described herein provide numerous advantages over current PCR techniques such as the use of lower amounts of reagents (e.g., reduced amounts of polymerase). Additionally, the methods described herein require significantly shorter reaction times (e.g., 35 minutes) compared to conventional PCR techniques (minimum 2 hours). The fact that the methods require no heat and shorter reaction times means there is less opportunity for degradation and formation of side-products. Indeed, as shown in the Examples below, the methods described herein amplify more DNA compared to conventional PCR techniques. As discussed above, conventional PCR requires controlled heating steps at every stage, which adds to the overall cost and inefficiency of the amplification process. Moreover, the use or primers and polymerases is optional, which further reduces the cost associated with PCR. Finally, the methods described herein produce nucleic acids that are more pure than conventional PCR. This feature is particularly important in applications where the nucleic acid is used in a comparative study (e.g., forensics where DNA at a crime site is compared to a suspect's DNA). In summary, the methods and devices described herein provide a more efficient and cost-effective way to perform PCR when compared to current PCR techniques.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions. The device used to prepare these examples was the amplification device 50 described above and shown in FIGS. 1-9.

Materials and Methods

Sample Treatment

All plasmid sequences used during analysis were provided and synthesized by Clonetex Systems Inc. Austin, Tex. 78756. USA. Genomic DNA was isolated in laboratory with QIAGEN standard purification kits. Polyadenylated 1.2 kb RNA transcript used as a control template for the cDNA synthesis reaction was purchased from Promega (Reverse Transcription System A3500 Promega). PCR thin wall tubes were used during all experimentation and inside the system to ensure that potential energy have an effect on the sample. Different types of DNA were tested to demonstrate the methods described herein can perform the same if not better than standard PCR. All DNA concentrations were measured with a standard nano-view spectrophotometer GE nanospectrophotometer (GE Healthcare Biosciences, P.O. Box 643065 Pittsburgh, Pa. 15264-3065), and also with regular standard UV/visual spectrophotometer within a 260/280 wave length (GE Healthcare Biosciences P.O. Box 643065 Pittsburgh, Pa. 15264-3065).

Plasmid DNA

Linear Plasmid:

A pBSK plasmid containing an iron promoter (3957 bp) was linearized with a standard digestion protocol with PsiI enzyme purchased from NEB, (New England Biolabs inc. R0657L) for 2.5 hours at 37° C. with alkaline phosphatase treatment. The final linearized plasmid concentration was 3.3 ng/µl. Sodium binding protein gene sequence was amplified with pUC/m13 forward and reverse primers from Promega, which amplified the sequences between the vector cloning site. The gene synthesis of the plasmids was performed by annealing complementary oligonucleotides. A high fidelity enzyme primer extension and T4 ligase were used for extension and ligation, respectively. The forward primer was pUC M13 (GTTTTCCCAGTC) (SEQ ID NO. 1) and the reverse primer was pUC M13 (CAGGAAACAGCT) (SEQ ID NO. 2). Both primers were synthesized by Clonetex Systems Inc. Recombinant Taq DNA was used as the polymerase.

Table 7 shows the results of thermal-free electromagnetic PCR without the use of polymerase an/or primers for DNA amplification compared to conventional thermocycler PCR without the use of polymerase and/or primers. pBSK plasmid containing magnesium BP (5574 bp) at an initial DNA concentration of 5.3 ng/µl was used in the experiments. The thermal-free electromagnetic PCR was run in 30 minutes, and conventional thermocycler PCR was run in 2 hours and 45 minutes.

When DNA amplification was performed in the presence of primers but in the absence of polymerase, the thermal-free electromagnetic PCR enhanced DNA amplification was 6-fold compared to conventional thermocycler PCR, which only enhanced DNA amplification 2-fold.

When DNA amplification was performed in the presence of polymerase but in the absence of primers, the thermal-free electromagnetic PCR enhanced DNA amplification was 3-fold compared to conventional thermocycler PCR, which only enhanced the DNA amplification 2-fold.

Finally, when DNA amplification was performed in the absence of both polymerase and primers, the thermal-free electromagnetic PCR and thermocycler PCR enhanced DNA amplification by 2-fold; however, DNA amplification using the thermal-free electromagnetic PCR was performed in 30 minutes compared to two hours and 45 minutes for the conventional thermocycler PCR.

TABLE 7

| DNA amplification methods | DNA amplification (concentration: ng/µl) | Percentage of DNA amplification |
|---|---|---|
| Initial DNA | Mean: 5.3 +/−SD: 2.8 | |
| Thermocylcler PCR | Mean: 8.0 +/−SD: 5.8 | 33.7% |
| Electromagnetic PCR 1 without polymerase (30 minutes) | Mean: 30.75 +/−SD: 0.4 | 82.8% |
| Electromagnetic PCR 1 without primers (30 minutes) | Mean: 17.5 +/−SD: 0.2 | 69.7% |
| Electromagnetic PCR 1 without polymerase and primers (30 minutes) | Mean: 9.25 +/−SD: 0.3 | 92.03% |

Coiled Plasmid:

A pYES plasmid vector containing the sequence of YDL194W gene of 2660 bp (Clontex) was amplified with designed primers to amplify the YDL194W gene sequence and backbone vector. This gene sequence was provided and synthesized by Clonetex Systems Inc. Austin, Tex. 78756. USA as described above. The incorporation of the sequence in the pYES plasmid was performed by cloning the gene into modified vector pYES by blunt-end ligation at the SmaI or EcoRV sites. The sample had an initial DNA concentration of 2.25 ng/µl.

A pYES plasmid holding Tocopherol phytyltransferase (PT) at an initial concentration of 2.25 µg/µl was amplified by thermal-free electromagnetic PCR from 1 minute to 150 minutes as compared to conventional thermocycler PCR (150 minutes). The results are provided in Table 8, where the results are an average of three runs. Referring to Table 8, when conventional thermocycler PCR was used, the percentage of DNA amplification was 97.4% and the rate of amplification was 38.5 times (i.e., cycles). When thermal-free electromagnetic PCR was used, the percentage of DNA amplification and rate of amplification was comparable if not better than conventional thermocycler PCR over the range of 1 minute to 150 minutes, with best results observed at 30 minutes.

TABLE 8

| DNA amplification methods | DNA amplification (concentration: ng/µl) | Percentage of DNA amplification | Rate of amplification |
|---|---|---|---|
| Initial DNA from Tocopherol in PYES | Mean: 2.25 +/−SD: 0 | | |
| Thermocylcler PCR | Mean: 86.6 +/−SD: 8.8 | 97.4% | 38.5 |
| Electromagnetic PCR 1 minute | Mean: 95.1 +/−SD: 19.9 | 97.6% | 42.3 |
| Electromagnetic PCR 2 minutes | Mean: 59.75 +/−SD: 21.2 | 96.2% | 26.5 |
| Electromagnetic PCR 5 minutes | Mean: 72.85 +/−SD: 5.1 | 92.03% | 12.5 |
| Electromagnetic PCR 15 minutes | Mean: 86.95 +/−SD: 12.2 | 97.4% | 38.6 |
| Electromagnetic PCR 30 minutes | Mean: 113.8 +/−SD: 13.9 | 98.0% | 50.6 |
| Electromagnetic PCR 60 minutes | Mean: 82.1 +/−SD: 7.1 | 97.2% | 36.5 |
| Electromagnetic PCR 120 minutes | Mean: 62.8 +/−SD: 7.7 | 96.4% | 27.9 |
| Electromagnetic PCR 150 minutes | Mean: 71.0 +/−SD: 11.5 | 96.8% | 31.6 |

PCR samples from pYES vector after amplification by thermal-free electromagnetic PCR were compared to conventional temperature-based PCR by gel electrophoresis. The bands from thermal-free electromagnetic PCR at different amplification times were more pronounced compared to the conventional temperature-based PCR (i.e., thermocycler control). Thus, the thermal-free electromagnetic PCR is more efficient with respect to DNA amplification compared to conventional thermocycler PCR.

Genomic DNA

Bacillus subtilis (Ehrenberg) Cohn ATCC number 82 was incubated for 18 hours and was used at a cell concentration 0.1 optical density (O.D). The DNA was extracted and purified with QIAGEN DNeasy Blood & Tissue Total DNA purification kit. Extracted genomic DNA resulted in a DNA concentration of 0.072 ng/µl. Sample amplification with random hexamers, from Promega C1181 was carried out.

Pure Bacillus subtilis DNA at an initial concentration of 14.2 ng/µl was amplified by thermal-free electromagnetic PCR from 1 minute to 150 minutes as compared to conventional thermocycler PCR (150 minutes). The results are provided in Table 9, where the results are an average of three runs. Referring to Table 9, when conventional thermocycler PCR was used, the percentage of DNA amplification was 84.8% and the rate of amplification was 6.6 times. When thermal-free electromagnetic PCR was used, the percentage of DNA amplification and rate of amplification was comparable if not better than conventional thermocycler PCR over the range of 1 minute to 150 minutes.

TABLE 9

| DNA amplification methods | DNA amplification (concentration: ng/µl) | Percentage of DNA amplification | Rate of amplification |
|---|---|---|---|
| Initial DNA (pure genomic DNA from Bacillus Subtilis) | Mean: 14.2 +/−SD: 0 | | |
| Thermocylcler PCR (150 minutes) | Mean: 93.8 +/−SD: 12.7 | 84.8% | 6.6 |
| Electromagnetic PCR 2 minutes | Mean: 107.5 +/−SD: 35.5 | 86.8% | 7.5 |
| Electromagnetic PCR 5 minutes | Mean: 67.4 +/−SD: 10 | 77.9% | 4.7 |
| Electromagnetic PCR 15 minutes | Mean: 113.6 +/−SD: 18.1 | 87.5% | 8.0 |
| Electromagnetic PCR 30 minutes | Mean: 75.8 +/−SD: 3.8 | 81.2% | 5.3 |
| Electromagnetic PCR 60 minutes | Mean: 115.3 +/−SD: 22.4 | 87.6% | 8.1 |
| Electromagnetic PCR 120 minutes | Mean: 79.1 +/−SD: 5.1 | 82.0% | 5.5 |
| Electromagnetic PCR 150 minutes | Mean: 83.1 +/−SD: 12.7 | 82.9% | 5.8 |

PCR samples of genomic DNA after amplification by thermal-free electromagnetic PCR were compared to conventional temperature-based PCR by gel electrophoresis. The bands from thermal-free electromagnetic PCR at different amplification times are more pronounced compared to the conventional temperature-based PCR (i.e., thermocycler control). Thus, the thermal-free electromagnetic PCR is more efficient with respect to genomic DNA amplification compared to conventional thermocycler PCR.

Amplification of DNA Marker

The DNA marker (1 Kb) was synthesized by Clonetex Systems Inc. Austin, Tex. 78756. USA Pure DNA marker at an initial concentration of 5.8 ng/µl was amplified by thermal-free electromagnetic PCR from 1 minute to 30 minutes as compared to conventional thermocycler PCR (150 minutes). The results are provided in Table 10, where the results are an average of three runs. Referring to Table 10, when conventional thermocycler PCR was used, the percentage of DNA amplification was 80.6% and the rate of amplification was 5.2 times. When thermal-free electromagnetic PCR was used, the percentage of DNA amplification and rate of amplification was comparable if not better than conventional thermocycler PCR over the range of 2 minutes to 30 minutes.

TABLE 10

| DNA amplification method | DNA amplification (concentration: ng/µl) | Percentage of DNA amplification | Rate of amplification |
|---|---|---|---|
| Initial DNA from pure DNA marker (1 kb) | Mean: 5.8 +/−SD: 0 | | |
| Thermocylcler PCR | Mean: 30 +/−SD: 4.5 | 80.6% | 5.2 |
| Electromagnetic PCR 1 minute | Mean: 19.5 +/−SD: 1.7 | 70.3% | 3.3 |
| Electromagnetic PCR 2 minutes | Mean: 50.3 +/−SD: 5.9 | 88.5% | 8.7 |
| Electromagnetic PCR 3 minutes | Mean: 69.2 +/−SD: 7.6 | 91.6% | 11.9 |
| Electromagnetic PCR 5 minutes | Mean: 34.2 +/−SD: 5.9 | 83.0% | 5.9 |
| Electromagnetic PCR 15 minutes | Mean: 90.8 +/−SD: 11.7 | 93.6% | 15.6 |
| Electromagnetic PCR 30 minutes | Mean: 59.5 +/−SD: 18.0 | 90.3% | 10.3 |

PCR samples of DNA marker after amplification by thermal-free electromagnetic PCR were compared to conventional temperature-based PCR by gel electrophoresis. The bands from thermal-free electromagnetic PCR at different amplification times are more pronounced compared to the conventional temperature-based PCR (i.e., thermocycler control). Thus, the thermal-free electromagnetic PCR is more efficient with respect to amplification of the DNA marker compared to conventional thermocycler PCR.

Transformation

Invitrogen Escherichia coli Top10 Chemically competent cells were used to transform pYES plasmid holding Tocopherol phytyltransferase (PT) amplified by thermal-free electromagnetic PCR and conventional temperature-based PCR. E. coli was transformed according to Promega Transformation protocol, California, USA.

The transformation results are provided in Table 11, where the results are an average of three plates. Referring to Table 11, when E. coli was transformed with PT amplified by conventional thermocycler PCR, the number of colony forming units was 3.3 to 4.0 over 16 to 48 hours. When E. coli was transformed with PT amplified by thermal-free electromagnetic PCR, the number of colony forming units was 23 to 26 over 16 to 48 hours. In summary, a significantly higher number E. coli colonies transformed with plasmid amplified by thermal-free electromagnetic PCR as compared to the lower number of colonies transformed with plasmid amplified by conventional thermocycler PCR.

TABLE 11

| DNA | Colony forming units at 16 hours | Colony forming units at 24 hours | Colony forming units at 32 hours | Colony forming units at 48 hours |
|---|---|---|---|---|
| DNA from Thermocylcler PCR of Tocopherol PT | Mean: 3.3 +/−SD: 1.2 | Mean: 4.0 +/−SD: 2.1 | Mean: 4.0 +/−SD: 2.1 | Mean: 4.0 +/−SD: 2.1 |

TABLE 11-continued

| DNA | Colony forming units at 16 hours | Colony forming units at 24 hours | Colony forming units at 32 hours | Colony forming units at 48 hours |
|---|---|---|---|---|
| DNA from electromagnetic PCR (15 minutes) of Tocopherol PT | Mean: 23.0 +/−SD: 2.1 | Mean: 24.3 +/−SD: 2.0 | Mean: 26.0 +/−SD: 2.9 | Mean: 26.0 +/−SD: 2.9 |
| Control DNA without amplification from Tocopherol PT in plasmid PYES | Mean: 7.3 +/−SD: 6.9 | Mean: 8.0 +/−SD: 7.8 | Mean: 11.6 +/−SD: 13.0 | Mean: 11.6 +/−SD: 13.0 |

Evaluation of Amplified Nucleic Acids

The amplification products produced by the methods described herein were evaluated. The estrogen sequence used for DNA amplification in this experiment is derived from human (*Homo sapiens*) (accession number AF 258491), and it was synthesized by Clontex System Inc (Austin, Tex.). Each amplification experiment was performed three times. The following protocol was used to purify the DNA produced from the thermocycler and electromagnetic PCR:

1. Add an equal volume of Membrane Binding Solution to the PCR gel slices. Heat samples at 50° C. until the gel is completely dissolved.
2. Insert SV Mini column into Collection Tube. Transfer prepared PCR product to the Mini column assembly. Incubate at room temperature for 1 minute.
3. Centrifuge at 16,000×g for 1 minute. Discard flow through and reinsert Mini column into Collection Tube. 4. Add 700 µl Membrane Wash Solution. Centrifuge at 16,000×g for 1 minute. Discard flow through and reinsert Mini column into Collection Tube. Repeat this step with 500 µl Membrane Wash Solution. Centrifuge at 16,000×g for 2 minutes. 5. Elute DNA with 100 µl of nuclease free water. Store at −20° C.

The results are provided in Table 12, which confirms that the PCR product after electromagnetic PCR is authentic and conserved. The concentration is preserved and still higher than the DNA concentration produced by conventional thermocycler PCR. Also, the electrophoretic gel showed good bands, which were larger and brighter than the conventional PCR gel. Finally, the DNA used is an estrogen sequence derived from human DNA. Thus, the electromagnetic PCR techniques are able to effectively amplify human DNA.

TABLE 12

DNA Amplification of Estrogen Receptor by Thermocycler and Electromagnetic PCR

| DNA amplification methods | DNA amplification (concentration: ng/µl) Mean +/− SD | Percentage of DNA amplification |
|---|---|---|
| Initial DNA from Estrogen Receptor | Mean: 19.63 +/−SD: 0 | |
| Thermal cycler PCR | Mean: 29.05 +/−SD: 2.5 | 47.9% |
| Electromagnetic PCR 2 minutes | Mean: 30.94 +/−SD: 1.2 | 57.6% |
| Electromagnetic PCR 15 minutes | Mean: 30.64 +/−SD: 5.9 | 56.1% |
| Electromagnetic PCR 30 minutes | Mean: 41.44 +/−SD: 3 | 111.0% |
| Electromagnetic PCR 60 minutes | Mean: 29.70 +/−SD: 2.2 | 51.3% |

Summary

The methods described herein are able to amplify DNA up to 4.5 fold more than conventional PCR methods. These results were obtained within a very short time (35 minutes), after several trials in which exposure to specific current during different experiments showed the exact time DNA samples needed to denature, anneal and elongate. Different currents were used in each step of the amplification process ranging from 250 mv and 125 mA, to 500 mV and 250 mA, 800 mV and 400 mA, 900 mV and 450 mA, 1000 mV 500 mA and 1250 mV and 650 mA showing consistent results. The best amplification results were obtained with the current of 900 mV and 450 mA. The present invention showed effective amplification results for different kinds of samples, including linear and coiled plasmids with a starting DNA concentration of 5 ng/µl, genomic DNA amplification with random primers, and with cDNA amplification processes. Targets of different sizes were tested, all showing consistent amplification results. Successful transformation cells with amplified DNA produced by the methods described herein were achieved as wells as effective digestion and further standard PCR amplification of the amplified product, which showed there was no DNA damage during the new amplification process.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A device for amplifying at least one sample of nucleic acid, comprising:
a circuit including at least one conductor through which a current is passed to induce a magnetic field;
a container support adapted to support at least one container of the nucleic acid sample, wherein at least a portion of the container and the sample are positioned within the magnetic field, and wherein the device includes no heating element that the sample is exposed to other than the magnetic-field-inducing circuit; and
a control unit adapted to control the current and the induced magnetic field, wherein the nucleic acid sample is amplified in response to being subjected to the magnetic field, and wherein the magnetic-field-inducing circuit is adapted and operated so that the current is a mini-current and the nucleic-acid amplification is thermal-free.

2. The nucleic-acid amplification device of claim 1, wherein the control unit is adapted to operate the magnetic-field-inducing circuit at a current of about 0.8 A to about 1.0 A to induce a magnetic field of about 0.322 Gauss to about 0.402 Gauss as applied to the sample at a centerline of the container of the sample.

3. The nucleic-acid amplification device of claim 1, wherein the at least one container comprises a plurality of vials, the at least one nucleic acid sample comprises a plurality of nucleic acid samples in the vials, and the device is adapted for batch processing the plurality of nucleic acid samples, and wherein the container support comprises a vial support, the vial support includes an array of holes that each receive a respective one of the vials, the array of holes includes a plurality of rows of the holes, the holes each define a respective center, and the conductor of the magnetic-field-inducing circuit is routed in a position spaced equidistant from each of the hole centers of a closest one of the rows of holes so that the magnetic field is uniformly applied to all of the samples in all of the vials.

4. The nucleic-acid amplification device of claim 3, wherein the conductor of the magnetic-field-inducing circuit is positioned below the vial support and routed centrally between every other one of the rows of the holes.

5. The nucleic-acid amplification device of claim 1, wherein the at least one container comprises at least one tube having a working portion through which the nucleic acid sample flows and the device is adapted for continuous processing, and wherein the container support comprises a tube support, and the conductor of the magnetic-field-inducing circuit and the tube working portion are positioned equidistantly from each other along entire lengths thereof to provide a uniform exposure of the nucleic acid sample in the tube working portion to the magnetic field.

6. The nucleic-acid amplification device of claim 5, wherein the conductor of the magnetic-field-inducing circuit is positioned below the tube support and the tube working portion is positioned above the tube support, with the conductor and tube working portion vertically aligned in conforming arrangements.

7. A method for amplifying a nucleic acid, the method comprising exposing a sample comprising the nucleic acid to a magnetic field using the device of claim 1.

8. The method of claim 7, wherein the sample comprising the nucleic acid further comprises a primer, a polymerase, or a combination thereof.

9. A device for amplifying at least one sample of nucleic acid, comprising:
a circuit including at least one conductor through which a mini-current is passed to induce a magnetic field;
at least one tube having a working portion through which the nucleic acid sample flows for continuous processing of the sample;
a tube support adapted to support the tube working portion, and the nucleic acid sample carried therein, within the magnetic field; and
a control unit adapted to control the mini-current and the induced magnetic field, wherein the nucleic acid sample is amplified in response to being subjected to the magnetic field,
wherein the conductor of the magnetic-field-inducing circuit and the tube working portion are positioned to provide a uniform exposure of the nucleic acid sample in the tube working portion to the magnetic field, wherein the device includes no heating element that the sample is exposed to other than the magnetic-field-inducing circuit, and wherein the magnetic-field-inducing circuit is adapted so that the nucleic-acid amplification is thermal-free.

10. The nucleic-acid amplification device of claim 9, wherein the control unit is adapted to operate the magnetic-field-inducing circuit at a mini-current of about 0.8 A to about 1.5 A to induce a magnetic field of about 0.322 Gauss to about 0.61 Gauss as applied to the sample at a centerline of the container of the sample.

11. The nucleic-acid amplification device of claim 9, wherein the control unit is adapted to operate the magnetic-field-inducing circuit at a mini-current of about 0.005 A to about 1.0 A to induce a magnetic field of about 0.001 Gauss to about 0.402 Gauss.

12. The nucleic-acid amplification device of claim 9, wherein the conductor of the magnetic-field-inducing circuit and the tube working portion are positioned equidistantly from each other along entire lengths thereof to provide a uniform exposure of the nucleic acid sample in the tube working portion to the magnetic field.

13. The nucleic-acid amplification device of claim 12, wherein the conductor of the magnetic-field-inducing circuit is positioned below the tube support and the tube working portion is positioned above the tube support, with the conductor and tube working portion vertically aligned in conforming arrangements.

14. The nucleic-acid amplification device of claim 12, wherein the tube working portion is arranged in serpentine configuration and the conductor is arranged in a conforming serpentine configuration so that they are vertically aligned and equidistantly separated along their entire lengths.

15. The nucleic-acid amplification device of claim 9, wherein the control unit include a pumps for flowing the nucleic acid sample through the tube working portion.

16. The nucleic-acid amplification device of claim 9, wherein the tube includes an inlet and an outlet at opposite ends of the tube working portion, the inlet includes a removable closure and is connectable to a sample tank, the outlet includes a removable closure and is connectable to a post-amplification device, and the tube has a diameter and a length selected to provide a predetermined residence time of the sample in the magnetic field for a given sample flow rate; wherein the control unit includes at least one input, at least one output, and at least one programmed processor; further comprising a housing for at least the magnetic-field-inducing circuit, the tube working portion, and the tube support; and further comprising a cooling system including a fan operable by the control unit.

17. A method for amplifying a nucleic acid, the method comprising exposing a sample comprising the nucleic acid to a magnetic field using the device of claim 16.

18. The method of claim 17, wherein the sample comprising the nucleic acid further comprises a primer, a polymerase, or a combination thereof.

19. The nucleic-acid amplification device of claim 1, further comprising a cooling system operable to dissipate from the sample any heat generated by the magnetic-field-inducing circuit.

* * * * *